United States Patent
Chiozza et al.

(10) Patent No.: US 11,970,703 B2
(45) Date of Patent: Apr. 30, 2024

(54) TRANSGENIC SAFFLOWER EVENT STACK IND-1ØØØ3-4 X IND-1ØØ15-7 AND METHODS TO USE IT

(71) Applicant: AG Biomolecules LLC, Wilmington, DE (US)

(72) Inventors: Mariana Chiozza, Ames, IA (US); Carlos Dezar, Paraná (AR); Patricia Miranda, Rosario (AR); Lucas Paultroni, Rosario (AR); Martin Salinas, Rosario (AR)

(73) Assignee: AG BIOMOLECULES LLC, Wilmington, DE (US)

( * ) Notice: Subject to any disclaimer, the term of this patent is extended or adjusted under 35 U.S.C. 154(b) by 0 days.

(21) Appl. No.: 17/948,381

(22) Filed: Sep. 20, 2022

(65) Prior Publication Data

US 2023/0082847 A1    Mar. 16, 2023

Related U.S. Application Data

(62) Division of application No. 16/998,742, filed on Aug. 20, 2020.

(51) Int. Cl.
*C12N 15/82*    (2006.01)
*C12Q 1/6895*   (2018.01)

(52) U.S. Cl.
CPC ....... *C12N 15/8257* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | | |
|---|---|---|---|
| 7,390,936 B1 | 6/2008 | Van Rooijen et al. | |
| 11,266,151 B2* | 3/2022 | Bowen | C12N 15/75 |
| 2008/0301832 A1* | 12/2008 | Kubo | C12N 15/1079 |
| | | | 800/278 |

OTHER PUBLICATIONS

GenBank Accession No. GS895965.1 (version 1 dated Feb. 9, 2014 entitled "SAX3D05 Flanking Sequence Tag of *Oryza sativa* T-DNA insertion lines *Oryza sativa* Japonic Group genomic, genomic survey sequence"; 2 total pages) (Year: 2014).*

(Continued)

*Primary Examiner* — Matthew R Keogh
*Assistant Examiner* — Rebecca Stephens
(74) *Attorney, Agent, or Firm* — Crowell & Moring LLP

(57) ABSTRACT

The present invention relates to a safflower plant or part thereof involving the molecular stacking of safflower events IND-1ØØØ3-4 x IND-1ØØ15-7, wherein the plant produces and accumulates chymosin in seed under agricultural conditions. A plant seed involving the molecular stacking of safflower events IND-1ØØØ3-4 x IND-1ØØ15-7. A consumer product produced from the seed, defined as chymosin, and additionally as ground grain, flour, flakes, oil, biodiesel, biogas, or another biomaterial. Also, the present invention include a recombinant DNA molecule involved in the molecular stacking of safflower events IND-1ØØØ3-4 x IND-1ØØ15-7. A DNA polynucleotide primer molecule comprising at least 15 contiguous nucleotides of the DNA molecule involved in the molecular stacking of safflower events IND-1ØØØ3-4 x IND-1ØØ15-7, or its complement which is useful in a DNA amplification method to produce a diagnostic amplicon for the event IND-1ØØØ3-4 and IND-1ØØ15-7, or each of them separately IND-1ØØØ3-4 and IND-1ØØ15-7. A vector of functional expression in plants and the microorganism that comprises it. A DNA detection kit comprising at least one DNA molecule comprising a nucleotide sequence with a sufficient length of (Continued)

contiguous nucleotides of the recombinant DNA molecule involved in the molecular stacking of safflower events IND-1ØØØ3-4 x IND-1ØØ15-7. Furthermore, the present invention involves methods of producing a safflower plant that accumulates chymosin in seeds under agricultural conditions; methods of producing a chymosin-producing safflower plant; methods to detect the presence of DNA corresponding to the molecular stack of safflower events IND-1ØØØ3-4 x IND-1ØØ15-7, or each of them separately IND-1ØØØ3-4 and IND-1ØØ15-7; methods for determining the zygosity of the safflower genome containing DNA from the molecular stack of safflower events IND-1ØØØ3-4 x IND-1ØØ15-7, or each of them separately IND-1ØØØ3-4 or IND-1ØØ15-7; and methods of producing a consumer product made from safflower.

3 Claims, 11 Drawing Sheets

Specification includes a Sequence Listing.

(56)  References Cited

OTHER PUBLICATIONS

GenBank Accession No. J01263.1 (version 1 dated Jun. 17, 1998 entitled "Phaseolus vulgaris beta-type phaseolin storage protein gene, complete cds"; 3 total pages). (Year: 1998).*

Mayerhofer et al. ("Introgression potential between safflower (Carthamus tinctorius) and wild relatives of the genus Carthamus" 2011 BMC Plant Biology 11:47 (10 total pages)). (Year: 2011).*

Office Action received in related U.S. Appl. No. 16/998,742 dated Mar. 14, 2023.

United States Non-Final Office Action issued in U.S. Appl. No. 16/998,742 dated Oct. 3, 2022 (26 pages).

Patial et al., "Development of an efficient, genotype independent plant regeneration and transformation protocol using cotyledonary nodes in safflower", J. Plant Biochem. Biotechnol. (Oct.-Dec. 2016), Mar. 30, 2016, pp. 421-432, vol. 25, No. 4 (12 pages).

Pollock et al., "Production and pilot scale recovery of bovine chymosin B from safflower seed", abstract BIOT 308 for poster at the 232$^{nd}$ ACS National Meeting held Sep. 10-14, 2006 in San Francisco, California, 2006, (one (1) page).

Ying et al., "Agrobacterium tumefaciens-mediated transformation of safflower (Carthamus tinctorius L.) cv. 'Centennial'", Plant Cell Reports (1992), pp. 581-585, vol. 11 (five (5) pages).

U.S. Office Action received in U.S. Appl. No. 16,998,742, dated Jun. 29, 2023 (14 pages).

Knowles, P.F. and Ashri, A., "Wild Safflower in California: improvement of cultivated safflower through plant-breeding program to obtain desirable characteristics of wild sgecies," *California Agriculture*, 2 pages (1958).

* cited by examiner

SAFFLOWER TRANSGENIC EVENT IND-10003-4 X IND-10015-7

FIG. 7A

TTAAAAACAAGCTCCTTCCATGTATGAAAAAAACCCTCTCAAACAAAAAACTTCTCAAGCTATACAGACACA
GATTAATCCACACAAACAACTTTATCCATACATGACTTGATGGAAACCAACAACTTCTTAGAGACGGA
TATATGTTCAAGAACATTACCAGCCAAACACTGATAGTTTAAACTGAAGGCGGGAAACGACAATCTGATCCAA
GCTCAAGCTGCTCTAGCATTCGCCATTCAGGCTGCGCAACTGTGTTGGGAAGGGCGATCGGTGCGGGCCTCTTCG
CTATTACGCCAGCTGGGGAAAGGGGATGTGCTGCAAGGGCGATTAAGTTGGGTAACGCCAGGGTTTCCCAGT
CACGACGTTGTAAAACGACGGCCAGTGCCAA

FIG. 7B

ATTAGGGTTCCTATAGGGTTTCGCTCTCATGTGTTGAGCATATAAGAAACCCTTAGTATGTATTTGTATTTGTAA
AATACTTCTATCAATAAAATTTCTAAATTCCTAAAACCAGTACTAAAATCCAGATCCCCGAATTAA
TTCGGCGTTAATTCAGTACATTAAAAACGTCCGCAATGTGTTATTAAGTTGTCTAAGCTAGGAACGCTTACG
AATGGCCCTTTGCCAGCATTCCGATCAAGCTCACTATCAGTCAGTTCGAACATGAAACAATGCAAAGTA
ATCCCAATCGATCCACCTTGTTTACGCTGCACAGAGAAACCCAAATTAAACTATGAAACTATTTTCTTCAC
CAACGTGCAAAGTACATCAATCCAACAATG

FIG. 7C

CAGCAATGCAATGTATAGAAAGTAAGTCCCGTTTGTTAGCAACTTAATGAGCTTAATAGGACTGAGAACTTAT
TCGGTCAGCTATAAATGACTGTGTGGTAGTTGGCTTGATGATATTGAAAGTGACTTATTCGTTAAGATTTACG
GGGGAGCTTTATGCAGAAATCCACAGAGTGCCAACCCACAGTGCCAACGTAATTCCAGTTACGGACTTACATACCA
AGAAAAGGTAAAAGCAATAAGAAATATGAAAATTAGTCCACCATAAATCTTATAGTTTATGGTTTAGGGTA
ACACTCTAACACTCTACTACTAATTACTTTAAACATTCTATAAACAATTTAAACATAGTAGAAT

FIG. 7D

TATCAATAAATTTCTAATTCCTAAAACCAAAATCCAGTACTAAAAATCCCCGAATTAATTCGGCGT
TAATTCAGTACATTAAAAACGTCCGCAATGTTATTAAGTTGTCTAAGCTCAATTGTTTACACCACAATA
AAAACCGTCCCAAAACAAAATCTTTTCGTCCTTACAGATTAATCCACACAAACATAGGACTTAATGAAAACC
AACCAAACAACCCTATTTGGTAAGCTTCTAGGGAGGAGCTTTATACAAAAAGCCATGATGATTTTCCTAGCCTA
CCCTCCCGGTTACAAAACACGCTAATTTCATCCACGAA

IND-10015-7 specific event detection system

IND-10015-7 WT allele

IND-10003-4 specific event detection system

IND-10003-4 WT allele

SEQUENCE LISTING

```
Sequence total quantity: 20
SEQ ID NO: 1              moltype = DNA  length = 7630
FEATURE                   Location/Qualifiers
misc_feature              1..7630
                          note = Insert and flanking regions IND-1XXX3-4
source                    1..7630
                          mol_type = other DNA
                          organism = synthetic construct
SEQUENCE: 1
cagttatgtt tggcttatca ctttaatcga tcacaattac accaaatgat tgacgacact   60
aaaatcacca acaaaccccc attatattac tctccaaaag aggccttaca aagaggggag  120
agtcccaaca tatatacaag tggctttctt tgtaagcttt ttgcataagc caaatagcta  180
tgagtctatt tggtcaacta tacatgactg tttggtagtg gcttaatgat atagaagttg  240
gcttattcaa aaagctttg gggtggaccg gccggggggg ggggtggggt gatgtagaaa  300
gccaagtttt tccaaacctg ccctctcga ttaaaaaaca agctccttcc atgtatgaaa  360
aaaccctctc aaacaaaaaa acttctcaag ctatacagac acagattaat ccacacaaac  420
aactttatcc atacatgact tgatggaaaa ccaaccaaca acttcttaga gacggatata  480
tgttcaagaa cattaccagc caaacactga tagtttaaac tgaaggcggg aaacgacaat  540
ctgatccaag ctcaagctgc tctagcattc gccattcagg ctgcgcaact gttgggaagg  600
gcgatcggtg cgggcctctt cgctattacg ccagtggcg aaaggggat gtgctgcaag  660
gcgattaagt tgggtaacgc cagggttttc ccagtcacga cgttgtaaaa cgacggccag  720
tgccaagctt gcatgcctgc aggaattcat tgtactccca gtatcattat agtgaaagtt  780
ttggctctct cgccggtggt ttttacctc tatttaaagg ggttttccac ctaaaaattc  840
tggtatcatt ctcactttac ttgttacttt aatttctcat aatctttgt tgaaattatc  900
acgcttccgc acacgatatc cctacaaatt tattatttgt taaacatttt caaaccgcat  960
aaaattttat gaagtcccgt ctatctttaa tgtagtctaa cattttcata ttgaaatata 1020
taatttactt aattttagcg ttggtagaaa gcataatgat ttattcttat tcttcttcat 1080
ataaatgttt aatatacaat ataaacaaat tcttaccttt aagaaggatt tcccattta  1140
tattttaaaa atatatttat caaatatttt tcaaccacgt aaatctcata ataataagtt 1200
gtttcaaaag taataaaatt taactccata atttttttat tcgactgatc ttaaagcaac 1260
acccagtgac acaactagcc atttttttct ttgaataaaa aaatccaatt atcattgtat 1320
```

```
tttttttata caatgaaaat ttcaccaaac aatgatttgt ggtatttctg aagcaagtca 1380
tgttatgcaa aattctataa ttcccatttg acactacgga agtaactgaa gatctgcttt 1440
tacatgcgag acacatcttc taaagtaatt ttaataatag ttactatatt caagatttca 1500
tatatcaaat actcaatatt acttctaaaa aattaattag atataattaa aatattactt 1560
ttttaatttt aagtttaatt gttgaatttg tgactattga tttattattc tactatgttt 1620
aaattgtttt atagatagtt taagtaaat ataagtaatg tagtagagtg ttagagtgtt 1680
accctaaacc ataaactata agatttatgg tggactaatt ttcatatatt tcttattgct 1740
tttacctttt cttggtatgt aagtccgtaa ctggaattac tgtgggttgc catggcactc 1800
tgtggtcttt tggttcatgc atggatgctt gcgcaagaaa aagacaaaga acaaagaaaa 1860
aagacaaaac agagagacaa aacgcaatca cacaaccaac tcaaattagt cactggctga 1920
tcaagatcgc cgcgtccatg tatgtctaaa tgccatgcaa agcaaacgt gcttaacatg 1980
cactttaaat ggctcaccca tctcaaccca cacacaaaca cattgccttt ttcttcatca 2040
tcaccacaac cacctgtata tattcattct cttccgccac ctcaatttct tcacttcaac 2100
acacgtcaac ctgcatatgc gtgtcatccc atgcccaaat ctccatgcat gttccaacca 2160
ccttctctct tatataatac ctataaatac ctctaatatc actcacttct ttcatcatcc 2220
atccatccag agtactacta ctctactact ataatacccc aacccaactc atattcaata 2280
ctactctacc atgaacttcc ttaagtcttt ccctttctac gctttccttt gtttcggtca 2340
atacttcgtt gctgttactc acgctgctga gatcacccgc attcctctct acaaaggtaa 2400
gtctctccgt aaggcgctga aggaacatgg acttctagaa gacttcttgc agaaacaaca 2460
gtatggcatc agcagcaagt actccggctt cggtgaagtt gctagcgtgc acttaccaa 2520
ctaccttgat agtcaatact ttgggaagat ctacctcgga accccgcctc aagagttcac 2580
cgttctcttt gatactggtt cctctgactt ctgggttccc tctatctact gcaagagcaa 2640
tgcctgcaag aaccaccaaa gattcgatcc gagaaagtcg tccaccttcc agaacttagg 2700
caaaccccttg tctatacact acggtacagg tagcatgcaa ggaatcttag gctatgatac 2760
cgtcactgtc tccaacattg tggacattca acagacagta ggacttagca cccaagaacc 2820
aggtgatgtc ttcacctatg cagaattcga tggcatcctt ggtatggcat acccatcgct 2880
cgcgtcagag tactcgatac ctgtgtttga caacatgatg aaccgacacc tagtagctca 2940
agacttgttc tcggtttaca tggacaggaa tggccaggag agcatgctca cgcttggagc 3000
tattgatcca tcctactaca caggatctct tcactgggtt ccagtcactg tgcagcagta 3060
ctggcaattc actgtggaca gtgtccaccat cagcggtggt gttgttgcat gtgaaggtgg 3120
atgtcaagct atcttggata ccggtacgtc caagctggtc ggacctagca gcgacattct 3180
caacattcag caagctattg gagccacaca gaaccagtac ggtgagtttg acatagattg 3240
cgacaacctt agctacatgc ctacagttgt ctttgagatc aacggcaaga tgtacccact 3300
gaccccctcc gcctatacca gccaggatca aggttctcgc accagtggat ttccagagtga 3360
gaaccattcc cagaaatgga tcttgggaga tgtgttcatt cgtgagtact acagcgtctt 3420
tgacagggcc aacaacctcg ttgggctagc taaagcaatc tgaccatgca tggatcaagc 3480
ttaaataagt atgaactaaa atgcatgtag gtgtaagagc tcatggagag catggaatat 3540
tgtatccgac catgtaacag tataaactaa gagctccatc tcacttcttc tatgaataaa 3600
caaaggatgt tatgatatt taacactcta tctatgcacc ttattgttct atgataaatt 3660
tcctcttatt attataaatc atctgaatcg tgacggctta tggaatgctt caaatagtac 3720
aaaaacaaat gtgtactata agactttcta acaattcta actttagcat tgtgaacgag 3780
acataagtgt taagaagaca taacaattat aatggaagaa gtttgtctcc atttatatat 3840
tatatattac ccacttatgt attatattag gatgttaagg agacataaca attataaaga 3900
gagaagtttg tatccatttta tatattat actaccatt tatatattat acttatccac 3960
ttatttaatg tctttataag gtttgatcca tgatatttct aatatttag ttgatatgta 4020
tatgaaaagg tactatttga actctcttac tctgtataaa ggttggatca tccttaaagt 4080
gggtctattt aattttattg cttcttacag ataaaaaaaa aattatgagt tggtttgata 4140
aaatattgaa ggatttaaaa taataataaa taataaataa catataatat atgtatataa 4200
atttattata atataacatt tatctataaa aaagtaaata ttgtcataaa tctatacaat 4260
cgtttagcct tgctggaacg aatctcaatt atttaaacga gagtaaacat atttgacttt 4320
ttggttattt aacaaattat tatttaacac tatatgaaat ttttttttttt tatcagcaaa 4380
gaataaaatt aaattaagaa ggacaatggt gtcccaatcc ttatacaacc aacttccaca 4440
agaaagtcaa gtcagagaca acaaaaaaac aagcaaagga aatttttaa tttgagttgt 4500
cttgtttgct gcataattta tgcagtaaaa cactacacat aacccttta gcagtagagc 4560
aatggttgac cgtgtgctta gcttctttta ttttattttt ttatcagcaa agaataaata 4620
aaataaaatg agacacttca gggatgtttc aaccccttata caaaccccca aaaacaagtt 4680
tcctagcacc ctaccaacta aggtaccgag ctcagaattc gaatccaaaa attacggata 4740
tgaatatagg catatccgta tccgaattat ccgtttgaca gctagcaacg attgtacaat 4800
tgcttcttta aaaaggaag aaagaaagaa agaaaagaat caacatcagc gttaacaaac 4860
ggccccgtta cggcccaaac ggtcatatag agtaacgcg ttaagcgttg aaagactcct 4920
atcgaaatac gtaaccgcaa acgtgtcata gtcagatccc ctcttccttc accgcctcaa 4980
acacaaaaat aatcttctac agcctatata taacccccc ccttctatct ctcctttctc 5040
acaattcatc atctttcttt ctctacccccc aattttaaga aatcctctct tctcctcttc 5100
attttcaagg taaatctctc tctctctctc tctctctctt attccttgtt ttaattaggt 5160
atgtattatt gctagtttgt taatctgctt atctttatgta tgcttatgt gaatatcttt 5220
atcttgttca tctcatccgt ttagaagcta taaatttgtt gatttgactg tgtatctaca 5280
cgtggtatg tttatatcta atcagatatg aatttcttca tattgttcg tttgtgtgta 5340
ccaatccgaa atcgttgatt tttttcattt aatcgtgtag ctaattgtac gtatacatat 5400
ggatctacgt atcaattgtt catctgtttg tgtttgtatg tatacagatc tgaaaacatc 5460
acttctctca tctgattgtg ttgttacata catagatata gatctgttat atcatttttt 5520
ttattaattg tgtatatata tatgtgcata gatctggatt acatgattgt gattatttac 5580
atgatttgt tatttacgta tgtatatatg tagatctgga cttttttggag ttgttgactt 5640
gattgtattt gtgtgtgtat atgtgtgttc tgatcttgat atgttatgta tgtgcagcca 5700
aggctacggg cgatccacca tgtctccgga gaggagacca gttgaatta ggcagctac 5760
agcagctgat atgccgcggg tttgtgatat cgttaaccat tacattgaga cgtctacagt 5820
gaactttagg acagagccac aaacaccaca agagtggatt gatgatctag agaggttgca 5880
agatagatac cctggttggg ttgctgaggt tgagggtgtt gtggctggta ttgcttacgc 5940
tgggccctgt aaggctagga acgcttacga ttggacagtg agagtactg tttacgtgtc 6000
acataggcat caaaggttgg gcctaggttc cacattgtac acacatttgc ttaagtctat 6060
```

```
ggaggcgcaa ggttttaagt ctgtggttgc tgttataggc cttccaaacg atccatctgt  6120
taggttgcat gaggctttgg gatacacagc ccggggtaca ttgcgcgcag ctggatacaa  6180
gcatggtgga tggcatgatg ttggttttg gcaaagggat tttgagttgc cagctcctcc  6240
aaggccagtt aggccagtta cccagatctg agtcgaccga atgagttcca agatggtttg  6300
tgacgaagtt agttggttgt ttttatggaa cttttgtttaa gctagcttgt aatgtggaaa  6360
gaacgtgtgg ctttgtggtt tttaaatgtt ggtgaataaa gatgtttcct ttggattaac  6420
tagtatttt cctattggtt tcatggtttt agcacacaac attttaaata tgctgttaga  6480
tgatatgctg cctgctttat tatttactta ccctcacct tcagtttcaa agttgttgca  6540
atgactctgt gtagtttaag atcgagtgaa agtagatttt gtctatattt attaggggta  6600
tttgatatgc taatggtaaa catggtttat gacagcgtac tttttggtt atggtgttga  6660
cgttccttt taaacattat agtagcgtcc ttggtctgtg ttcattggtt gaacaaaggc  6720
acactcactg ggagatgccg tctccactga tatttgaaca aagaattcgt aatcatgtca  6780
tagctgtttc ctgtgtgaaa ttgttatccg ctcacaattc cacacaacat acgagccgga  6840
agcataaagt gtaaagcctg gggtgcctaa tgagtgagct aactcacatt aattgcgttg  6900
cgctcactgc ccgctttcca gtcgggaaac ctgtcgtgcc agatcgaccc aagtaccgcc  6960
acctaacaat tcgttcaagc cgagatcggc ttcccggcct agagtcgatc gacaagctcg  7020
agtttctcca taataatgtg tgagtagttc ccagataagg gaattagggt tcctataggg  7080
tttcgctcat gtgttgagca tataagaaac ccttagtatg tatttgtatt tgtaaaatac  7140
ttctatcaat aaaatttcta attcctaaaa ccaaaatcca gtactaaaat ccagatcccc  7200
cgaattaatt cggcgttaat tcagtacatt aaaaacgtcc gcaatgtgtt attaagttgt  7260
ctaaggctag gaacgcttac gattggccct tttgccagca ttccgatcaa gctcactatc  7320
agtcaacggt tcgaacatga aacaatgcaa agtaatcccac cttgtttacg  7380
ctgcacagag aaacccaaat taaactatga acaatatttt tcttcaccac cgtgcaaaag  7440
tacatcaatc caacaatgcc aatagatcat ggcttaaaaa tagagttaaa attagttgat  7500
tgcctgaaac ttgtcacgat atagcttggc tgccatgcca tgggccagta acatgttgtg  7560
cataacaatg agaggctcaa cgtctgaatt ccagcaacaa cagttgccaa agggctctga  7620
acaacgagaa                                                          7630

SEQ ID NO: 2           moltype = DNA   length = 8324
FEATURE                Location/Qualifiers
misc_feature           1..8324
                       note = Insert and flanking regions IND-1XX15-7
source                 1..8324
                       mol_type = other DNA
                       organism = synthetic construct
SEQUENCE: 2
aaatggctca tttaggagct gtaacagcta actgggtaag agtgtgatct gggtaagtac   60
caactgaaat tggtttttac tgctaaaaga ttaccattat aaccctctga aaaacccttta  120
tcacaaaaag atggtagccc ttgaaagtgc gtaaactaga gacatgttgt tagcagctta  180
atgagcttaa tctggctcgc aacttattcg gtcagcaatg caatgtatag aaagtaagtc  240
ccgtttgtta gcaacttaat gagcttaata ggactgagaa cttattcggt cagctataaa  300
tgactgtgtg gtagttggct tgatgatatt gaaagtgact tattcgttaa gatttacggg  360
ggagctttat gcagaaatcc acagagtgcc atggcaacc agtaattc cagttacgga  420
cttacatacc aagaaaaggt aaaagcaata agaaatatat gaaaattagt ccaccataaa  480
tcttatagtt tatggtttag ggtaacactc taacactcta ctacattact tatatttact  540
ttaaactatc tataaaacaa tttaaacata gtagaataat aaatcaatag tcacaaattc  600
aacaattaaa cttaaaatta aaaaagtaat atttaatta tatctaatta atttttaga  660
agtaatattg agtatttgat atatgaaatc ttgaatatag taactattat taaaattact  720
ttagaagatg tgtctcgcat gtaaaagcag atcttcagtt acttccgtag tgtcaaatgg  780
gaattataga attttgcata acatgacttg cttcagaaat accacaaatc attgtttggt  840
gaattttca ttgtataaaa aaaatacaat gataattgga ttttttttat caaagaaaaa  900
aatggctagt tgtgtcactg ggtgttgctt taagatcagt cgaataaaa aattatggag  960
ttaaatttta ttacttttga aacaacttat tattatgaga tttacgtggt tgaaaaatat 1020
ttgataaata tattttaaa atataaaatg ggaaatcctt cttaaggtaa agaatttgtt 1080
tatattgtat attaaacatt tatatgaaga agaataagaa taaatcatta tgcttttctac 1140
caacgctaaa attaagtaaa ttatatattt caatatgaaa atgttagact acattaaaga 1200
tagacgggac ttcataaaat tttatgcggt ttgaaaatgt ttaacaaata ataaattgt 1260
agggatatcg tgtgcggaag cgtgataatt tcaaccaaag attatgagaa attaaagtaa 1320
caagtaaagt gagaagtgata ccagaattt taggtgaaa accccttta atagaggtaa 1380
aaaccaccg gcgagagagc caaaactttc actataatga tactgggagt acaatgaatt 1440
cctgcaggca tgcaagcttg gcactggccg tcgttttaca acgtcgtgac tgggaaaacc 1500
ctggcgttac ccaacttaat cgccttgcag cacatcccc tttcgccagc tggcgtaata 1560
gcgaagaggc ccgcaccgat cgcccttccc aacagttgcg cagcctgaat ggcgaatgct 1620
agagcgcgtt gagcttggat cagattgtcg tttcccgcct tcagtttaaa ctatcagtgt 1680
ttgaacactg atagttaa ctgaaggcgg gaaacgacaa tctgatccaa gctcaagctg 1740
ctctagcatt cgggaattca cgtttttctt tgaataaaaa aatccaatta tcattgtatt 1800
tttttatac aatgaaatt tcaccaaaca atgattgtg gtattctga agcaagtcat 1860
gttatgcaaa attctataat tcccatttga cactacggaa gtaactgaag atctgctttt 1920
acatgcgaga cacatcttct aaagtaattt taataatagt tactatattc aagatttcat 1980
atatcaaata ctcaatatta cttctaaaaa attaattaga tataattaaa atattacttt 2040
tttaattta agtttaattg ttgaatttgt gactattgat ttattattct actatgttta 2100
aattgtttta tagatagttt aaagtaaata taagtaatgt agtagagtgt tagagtgtta 2160
ccctaaacca taaactataa gatttatggt ggactaattt tcatatattt cttattgctt 2220
ttacctttc ttggtatgta agtccgtaac tggaattact gtgggttgcc atggcactga 2280
gtggtctttt ggttcatgca tggatgcttg cgcaagaaaa agacaaagaa caaagaaaaa 2340
agacaaaaca gagagacaaa acgcaatcac acaccaact caaattagtc actggctgat 2400
caagatcgcc gcgtccatgt atgtctaaat gccatgcaaa gcaacacgtg cttaacatgc 2460
actttaaatg gctcacccat ctcaacccac acacaaacac attgcctttt tcttcatcat 2520
caccacaaacc acctgtatat attcattctc ttccgccacc tcaatttctt cacttcaaca 2580
```

```
cacgtcaacc tgcatatgcg tgtcatccca tgcccaaatc tccatgcatg ttccaaccac 2640
cttctctctt atataatacc tataaatacc tctaatatca ctcacttctt tcatcatcca 2700
tccatccaga gtactactac tctactacta taatacccca acccaactca tattcaatac 2760
tactctacta tgaacttcct taagtctttc cctttctacg ctttcctttg tttcggtcaa 2820
tacttcgttg ctgttactca cgctgctgag atcacccgca ttcctctcta caaaggtaag 2880
tctctccgta aggcgctgaa ggaacatgga cttctagaag acttcttgca gaaacaacag 2940
tatggcatca gcagcaagta ctccggcttc ggtgaagttg ctagcgtgcc acttaccaac 3000
taccttgata gtcaatactt tgggaagatc tacctcggaa ccccgcctca agagttcacc 3060
gttctctttg atactggttc ctctgacttc tgggttccct ctatctactg caagagcaat 3120
gcctgcaaga accaccaaag attcgatccg agaaagtcgt ccaccttcca gaacttaggc 3180
aaacccttgt ctatacacta cggtacaggg agcatgcaag gaatcttagg ctatgatacc 3240
gtcactgtct ccaacattgt ggacattcaa cagacagtag gacttagcac ccaagaacca 3300
ggtgatgtct tcacctatgc agaattcgat ggcatccttg gtatggcata cccatcgctc 3360
gcgtcagagt actcgatacc tgtgtttgac aacatgatga accgacacct agtagctcaa 3420
gacttgttct cggtttacat ggacaggaat ggccaggaga gcatgctcac gcttggagct 3480
attgatccat cctactacac aggatctctt cactgggttc cagtcactgt gcagcagtac 3540
tggcaattca ctgtggacag tgtcaccatc agcggtgtgg ttgttgcatg tgaaggtgga 3600
tgtcaagcta tcttggatac cggtacgtcc aagctggtcg gacctagcag cgacattctc 3660
aacattcagc aagctattgg agccacacag aaccagtacg gtgagtttga catagattgc 3720
gacaacctta gctacatgcc tacagttgtc tttgagatca acggcaagat gtacccactg 3780
accccctccg cctataccag ccaggatcaa gggttctgca ccagtggatt ccagagtgag 3840
aaccattccc agaaatggat cttgggagat gtgttcattc gactagtacta cagcgtcttt 3900
gacagggcca acaacctcgt tgggctagct aaagcaatct gaccatgcat ggatcaagct 3960
taaataagta tgaactaaaa tgcatgtagg tgtaagagct catggagagc atggaatatt 4020
gtatccgacc atgtaacagt ataataactg agctccatct cacttcttct atgaataaac 4080
aaaggatgtt atgatatatt aacactctat ctatgcacct tattgttcta tgataaattt 4140
cctcttatta ttataaatca tctgaatcgt gacggcttat ggaatgcttc aaatagtaca 4200
aaaacaaatg tgtactataa gactttctaa acaattctaa ctttagcatt gtgaacgaga 4260
cataagtgtt aagaagacat aacaattata tggaagaag tttgtctcca tttatatatt 4320
atatattacc cacttatgta ttatattagg atgttaagga gacataacaa ttataaagag 4380
agaagtttgt atccatttat atattatata ctacccattt atatattata cttatccact 4440
tatttaatgt ctttataagg tttgatccat gatatttcta atattttagt tgatatgtat 4500
atgaaaaggt actatttgaa ctctcttact ctgtataaag gttggatcat ccttaaagtg 4560
ggtctattta attttattgc ttcttacaga taaaaaaaaa attatgagtt ggtttgataa 4620
aatattgaag gatttaaaat aataataaat aataaataac atatatata tgtatataaa 4680
tttattataa tataacattt atctataaaa aagtaaatat tgtcataaat ctatacaatc 4740
gtttagcctt gctggaacga atctcaatta tttaaacgag agtaaacata tttgactttt 4800
tggttattta acaaattatt atttaacact atatgaaatt tttttttttt atcagcaaag 4860
aataaaatta aattaagaag gacaatggtg tcccaatcct tatacaacca acttccacaa 4920
gaaagtcaag tcagagacaa caaaaaaaca agcaaaggaa attttttaat ttgagttgtc 4980
ttgtttgctg cataatttat gcagtaaaac actacacata acccttttag cagtagagca 5040
atggttgacc gtgtgcttag cttcttttat tttatttttt tatcagcaaa gaataaataa 5100
aataaaatga gacacttcag ggatgtttca acccttatac aaaacccccaa aaacaagttt 5160
cctagcaccc taccaactaa ggtaccgagc tcagaattcg aatccaaaaa ttacggatat 5220
gaatataggc atatccgtat ccgaattatc cgtttgacag ctagcaacga ttgtacaatt 5280
gcttcttaa aaaggaaga aagaaagaaa gaaaagaatc aacatcagcg ttaacaaacg 5340
gcccgttac ggcccaaacg gtcatataga gtaacgggct taagcgttga aagactccta 5400
tcgaaatacg taaccgcaaa cgtgtcatag tcagatcccc tcttcctcca ccgcctcaaa 5460
cacaaaaata atcttctaca gcctatatat acaaccccca cttctatctc tcctttctca 5520
caattcatca tctttctttc tctacccca attttaagaa atcctctctt ctcctcttca 5580
ttttcaaggt aaatctctct ctctctctct ctctctgtta ttccttgttt taattaggta 5640
tgtattattg ctagtttgtt aatctgctta tcttatgtat gccttatgtg aatatcttta 5700
tcttgttcat ctcatccgtt tagaagctat aaatttgttg atttgactgt gtatctacac 5760
gtggttatgt ttatatctaa tcagatatga atttcttcat attgttgcgt ttgtgtgtac 5820
caatccgaaa tcgttgattt tttcattta atcgtgtagc taattgtacg tatacatatg 5880
gatctacgta tcaattgttc atctgtttgt gtttgtatgt atacagatct gaaaacatca 5940
cttctctcat ctgattgtgt tgttacatac atagatatag atctgttata tcatttttt 6000
tattaattgt gtatatatat atgtgcatag atctggatta catgattgtg attatttaca 6060
tgattttgtt atttacgtat gtatatatgt agatctggac tttttggagt tgttgactg 6120
attgtatttg tgtgtgtata tgtgtgttct gatcttgata tgttatgtat gtgcagccaa 6180
ggctacgggc gatccaccat gtctccgag aggagaccag ttgagattag gccagctaca 6240
gcagctgata tggccgcggt ttgtgatatc gttaaccatt acattgagac gtctacagtg 6300
aactttagga cagagccaca aacaccacaa gagtggattg atgatctaga gaggttgcaa 6360
gatagatacc cttggttggt tgctgagtt gagggtgttg tggctggtat tgcttacgct 6420
gggccctgga aggctaggaa cgcttacgat tggacagttg agagtactgt ttacgtgtca 6480
catagggcatc aaaggtttggg cctaggttcc acattgtaca cacatttgct taagtctatg 6540
gaggcgcaag gttttaagtc tgtggttgct gttataggcc ttccaaacga tccatctgtt 6600
aggttgcatg aggctttggg atacacagcc cggggtacat tgcgcgcagc tggatacaag 6660
catggtggat ggcatgatgt tggttttttgg caaagggatt ttgagttgcc agctcctcca 6720
aggccagtta ggccagttac ccagatctga gtcgaccgaa tgagttccaa gatggtttgt 6780
gacgaagtta gttggttgtt tttatggaac tttgtttaag ctagcttgta atgtggaaag 6840
aacgtgtggc tttgtggttt ttaaatgttg gtgaataaag atgtttcctt tggattaact 6900
agtattttc ctattggttt catggtttta gcacacaaca ttttaaatat gctgttagat 6960
gtcgtcttgtc ctgcttttatt attttacttac ccctcaccctt cagtttcaaa gttgttgcaa 7020
tgactctgtg tagtttaaga tcgagtgaaa gtagattttg tctatattta ttaggggtat 7080
ttgatatgct aatggtaaac atgtttatg acagcgtact ttttggtta tggtgttgac 7140
gtttcctttt aaacattata gtagcgtcct tggtctgtgt tcattggttg aacaaaggca 7200
cactcacttg gagatgccgt ctccactgat atttgaacaa agaattcgta atcatgtcat 7260
agctgtttcc tgtgtgaaat tgttatccgc tcacaattcc acacaacata cgagccgaa  7320
```

```
gcataaagtg taaagcctgg ggtgcctaat gagtgagcta actcacatta attgcgttgc   7380
gctcactgcc cgctttccag tcgggaaacc tgtcgtgcca gatcgaccca agtaccgcca   7440
cctaacaatt cgttcaagcc gagatcggct tcccggccta gagtcgatcg acaagctcga   7500
gtttctccat aataatgtgt gagtagttcc cagataaggg aattagggtt cctataggg    7560
ttcgctcatg tgttgagcat ataagaaacc cttagtatgt atttgtattt gtaaaatact   7620
tctatcaata aaatttctaa ttcctaaaac caaaatccag tactaaaatc cagatcccc    7680
gaattaattc ggcgttaatt cagtacatta aaaacgtccg caatgtgtta ttaagttgtc   7740
taagcgtcaa tttgttaca ccacaataaa aaaccgtccc aaacaaaatc ttttccgtcc    7800
ttacagatta atccacacaa acataggact taatgaaaac caaccaaaca acccctattt   7860
ggtaagcttc tagggaggag ctttatacaa aaagccatga ttttcctag cctaccctc    7920
ccggttacaa acacgctaat ttcatccacg aaaaaactct ccaaaaaaaa atctttcgca   7980
gtgtatatag acagattaat caacacagac aactttata gtgcagaact aagtggaaaa   8040
tcagacgaac aaatgcacaa tatatattta aagaccatat atttacctca atggcgtcga   8100
ctgtgagagg caggacgatg actttctcag agaacttctg tttctcagct gcatcacgag   8160
caagccgacg acggtaagag aaattgttga acaaagctct gagctccttc agctttccct   8220
tagcaacagc caattcacga agtgcacgaa gagcctgaga tctcctgatc agataagccc   8280
taaaagtcat ctggatcacc atggctgcat cctgaggtga taac                   8324

SEQ ID NO: 3          moltype = DNA   length = 378
FEATURE               Location/Qualifiers
misc_feature          1..378
                      note = Right junction Sequence IND-1XXX3-4
source                1..378
                      mol_type = other DNA
                      organism = synthetic construct
SEQUENCE: 3
aaatggctca tttaggagct gtaacagcta actgggtaag agtgtgatct gggtaagtac     60
caactgaaat tggtttttac tgctaaaaga ttaccattat aaccctctga aaaaccctta    120
tcacaaaaag atggtagccc ttgaaagtgc gtaaactaga cattgttgt tagcagctta    180
atgagcttaa tctggctcgc aacttattcg gtcagcaatg caattgtatag aaagtaagtc   240
ccgtttgtta gcaacttaat gagcttaata ggactgagaa cttattcggt cagctataaa    300
tgactgtgtg gtagttggct tgatgatatt gaaagtgact tattcgttaa gatttacggg    360
ggagctttat gcagaaat                                                378

SEQ ID NO: 4          moltype = DNA   length = 580
FEATURE               Location/Qualifiers
misc_feature          1..580
                      note = Left junction Sequence IND-1XXX3-4
source                1..580
                      mol_type = other DNA
                      organism = synthetic construct
SEQUENCE: 4
cgtcaatttg tttacaccac aataaaaaac cgtcccaaac aaaatctttt ccgtccttac     60
agattaatcc acacaaacat aggacttaat gaaaaccaac caaacaaccc ctatttggta    120
agcttctagg gaggagcttt atacaaaaag ccatgatttt cctagcctag cccctcccgg    180
ttacaaaac gctaatttca tccacgaaaa aactctccaa aaaaaatct ttcgcagtgt    240
atatagacag attaatcaac acagacaact ttatatgtgc agaactaagt ggaaaatcag    300
acgaacaaat gcacaatata tatttaaaga ccatatattt acctcaatgg cgtcgactgt    360
gagaggcagg acgatgactt tctcagagaa cttctgtttc tcagctgcat cacgagcaag    420
ccgacgacg taagagaaat tgttgaacaa agctctgagc tccttcagct ttcccttagc    480
aacagccaat tcacgaagtg cacgaagagc ctgagatctc ctgatcagat aagccctaaa    540
agtcatctgg atcaccatgg ctgcatcctg aggtgataac                          580

SEQ ID NO: 5          moltype = DNA   length = 500
FEATURE               Location/Qualifiers
misc_feature          1..500
                      note = Right junction Sequence IND-1XX15-7
source                1..500
                      mol_type = other DNA
                      organism = synthetic construct
SEQUENCE: 5
cagttatgtt tggcttatca ctttaatcga tcacaattac accaaatgat tgacgacact     60
aaaatcacca acaaaccccc attatattac tctccaaaag aggccttaca agagggggag    120
agtcccaaca tatatacaag tggctttctt tgtaagcttt ttgcataagc caaatagcta    180
tgagtctatt tggtcaacta tacatgactg tttggtagtg gcttaatgat atagaagttg    240
gcttattcaa aaagctttg gggtggaccg gcgggggg ggggtggggt gatgtagaaa       300
gccaagtttt tccaaacctg cccctctcga ttaaaaaaca agctccttcc atgtatgaaa    360
aaaccctctc aaacaaaaaa acttctcaag ctatacagac acagattaat ccacacaaac    420
aactttatcc atacatgact tgatggaaaa ccaaccaaca acttcttaga gacggatata    480
tgttcaagaa cattaccagc                                                500

SEQ ID NO: 6          moltype = DNA   length = 365
FEATURE               Location/Qualifiers
misc_feature          1..365
                      note = Left junction Sequence IND-1XX15-7
source                1..365
                      mol_type = other DNA
                      organism = synthetic construct
SEQUENCE: 6
```

```
gctaggaacg cttacgattg gcccttttgc cagcattccg atcaagctca ctatcagtca    60
acggttcgaa catgaaacaa tgcaaagtaa tcccaatcga tccaccttgt ttacgctgca   120
cagagaaacc caaattaaac tatgaacaat attttt cttc accaacgtgc aaaagtacat   180
caatccaaca atgccaatag atcatggctt aaaaatagag ttaaaattag ttgattgcct   240
gaaacttgtc acgatatagc ttggctgcca tgccatgggc cagtaacatg ttgtgcataa   300
caatgagagg ctcaacgtct gaatt ccag caacacagtt gccaagggc tctgaacaac   360
gagaa                                                               365
```

```
SEQ ID NO: 7          moltype = DNA  length = 6765
FEATURE               Location/Qualifiers
misc_feature          1..6765
                      note = Insert Sequence
source                1..6765
                      mol_type = other DNA
                      organism = synthetic construct
SEQUENCE: 7
caaacactga tagtttaaac tgaaggcggg aaacgacaat ctgatccaag ctcaagctgc    60
tctagcattc gccattcagg ctgcgcaact gttgggaagg gcatcggtg cgggcctctt   120
cgctattacg ccagctggcg aaaggggggat gtgctgcaag gcgattaagt tgggtaacgc   180
cagggttttc ccagtcacga cgttgtaaaa cgacggccag tgccaagctt gcatgcctgc   240
aggaattcat tgtactccca gtcattat agtgaaagtt ttggctctct cgccggtggt   300
ttttacctc tatttaaagg ggttttccac ctaaaaattc tgtgatcatt ctcactttac   360
ttgttacttt aatttctcat aatctttggt tgaaattatc acgcttccgc acacgatatc   420
cctacaaatt tattatttgt taaacatttt caaaccgcat aaaatttat gaagtcccgt   480
ctatctttaa tgtagtctaa catttt cata ttgaaatata taatt tactt aattttagcg   540
ttggtagaaa gcataatgat ttattcttat tcttcttcat ataaaatgtt aatatacaat   600
ataaacaaat tctttacctt aagaaggatt tcccatttta tattt aaaaa atatatttat   660
caaatatttt tcaaccacgt aaatctcata ataataagtt gtttcaaaag taataaaatt   720
taactccata atttttttat tcgactgatc ttaaagcaac acccagtgac acaactagcc   780
attttttct ttgaataaaa aaatccaatt atcattgtat tttttttata caatgaaaat   840
ttcaccaaac aatgatttgt ggtatttctg aagcaagtca tgttatgcaa aattctataa   900
ttcccatttg acactacgga agtaactgaa gatctgcttt tacatgcgag acacatcttc   960
taaagtaatt ttaataatag ttactatatt caagatttca tatatcaaat actcaatatt  1020
acttctaaaa aattaattag atataattaa aatattactt ttttaatttt aagtttaatt  1080
gttgaatttg tgactattga tttattattc tactatgttt aaattgtttt atagatagtt  1140
taaagtaaat ataagtaatg tagtagagtg ttagagtgtt accctaaacc ataaactata  1200
agatttatgg tggactaatt ttcatatatt tcttattgct tttacctttt cttggtatgt  1260
aagtccgtaa ctggaattac tgtgggttgc catggcactc tgtggtcttt tggttcatgc  1320
atggatgctt gcgcaagaaa aagacaaaga acaaagaaaa aagacaaaac agagagacaa  1380
aacgcaatca cacaaccaac tcaaattagt cactggctga tcaagatcgc cgcgtccatg  1440
tatgtctaaa tgccatgcaa agcaacacgt gcttaacatg cactttaaat ggctcaccca  1500
tctcaaccca cacacaaaca cattgccttt ttcttcatca tcaccacaac cacctgtata  1560
tattcattct cttccgccac ctcaattt ct tcacttcaac acacgtcaac ctgcatatgc  1620
gtgtcatccc atgccaaat ctccatgcat gttccaacca ccttctctct tatataatac  1680
ctataaatac ctctaatatc actcacttct ttcatcatcc atccatccag agtactacta  1740
ctctactact ataatacccc aacccaactc atattcaata ctactctacc atgaacttcc  1800
ttaagtcttt cccttt ctac gctttccttt gtttcggtca atacttcgtt gctgttactc  1860
acgctgctga gatcacccgc attcctctct acaaaggtaa gtctctccgt aaggcgctga  1920
aggaacatgg acttctagaa gacttcttgc agaaacaaca gtatggcatc agcagcaagt  1980
actccggctt cggtgaagtt gctagcgtgc cacttaccaa ctaccttgat agtcaatact  2040
ttgggaagat ctacctcgga accccgcctc aagagttcac cgttctcttt gatactggtt  2100
cctctgactt ctgggttccc tctatctact gcaagagcaa tgcctgcaag aaccaccaaa  2160
gattcgatcc gagaaagtcg tccaccttcc agaacttagg caaacccttg tctatacact  2220
acggtacagg tagcatgcaa ggaatcttag gctatgatac cgtcactgtc tccaacattg  2280
tggacattca acagacagta ggacttagca cccaagaacc aggtgatgtc ttcacctatg  2340
cagaattcga tggcatcctt ggtatggcat acccatcgct cgcgtcagag tactcgatac  2400
ctgtgtttga caacatgatg aaccgacacc tagtagctca agacttgttc tcggtttaca  2460
tggacaggaa tggccaggag agcatgctca cgcttggagc tattgatcca tcctactaca  2520
caggatctct tcactgggtt ccagtcactg tgcagcagta ctggcaattc actgtggaca  2580
gtgtccaccat cagcggtgtg gttgttgcat gtgaaggtgg atgtcaagct atcttggata  2640
ccggtacgtc caagctggtc ggaccta gca gcgacattct caacattcag caagctattg  2700
gagccacaca gaaccagtac ggtgagtttg acatagattg cgacaacctt agctacatgc  2760
ctacagttgt ctttgagatc aacggcaaga tgtaccocact gacccccctcc gcctatacca  2820
gccaggatca agggttctgc accagtggat tccagagtga ccagcattcc cagaaatgca  2880
tcttgggaga tgtgttcatt cgtgagtact acagcgtctt tgacagggcc aacaacctcg  2940
ttgggctagc taaagcaatc tgaccatgca tggatcaagc ttaaaagt atgaactaaa  3000
atgcatgtag gtgtaagagc tcatggagag catggaatat tgtatccgac catgtaacag  3060
tataataact gagctccatc tcacttcttc tatgaataaa caaaggatgt tatgatatat  3120
taacactcta tctatgcacc ttattgttct atgataaatt tcctcttatt attataaatc  3180
atctgaatcg tgacggctta tggaatgctt caaatagtac aaaaacaaat gtgtactata  3240
agactttcta aacaattcta actttagcat tgtgaacgag acataagtgt taagaagaca  3300
taacaattat aatggaagaa gtttgtctcc atttatatat tatatattac ccacttatgt  3360
attatattag gatgttaagg agacataaca attataaaga gagaagtttg tatccattta  3420
tatatttat actacccatt tatatattat acttaatcc ttatttaatg tctttataag  3480
gtttgatcca tgatatttct aatatttttag ttgatatgta tatgaaaagg tactatttga  3540
actctcttac tctgtataaa ggttggatca tccttaaagt gggtctattt aattttattg  3600
cttcttacag ataaaaaaaaaaatttatgagt tggtttgata aaatattgaa ggatttaaaa  3660
taataataaa taataaataa catataatat atgtatataa atttattata ataacatt  3720
tatctataaa aaagtaaata ttgtcataaa tctatacaat cgtttagcct tgctggaacg  3780
```

```
aatctcaatt atttaaacga gagtaaacat atttgacttt ttggttattt aacaaattat   3840
tatttaacac tatatgaaat ttttttttt tatcagcaaa gaataaaatt aaattaagaa    3900
ggacaatggt gtcccaatcc ttatacaacc aacttccaca agaaagtcaa gtcagagaca   3960
acaaaaaaac aagcaaagga aatttttaa tttgagttgt cttgtttgct gcataattta    4020
tgcagtaaaa cactacacat aaccctttta gcagtagagc aatggttgac cgtgtgctta   4080
gcttctttta ttttatttt ttatcagcaa agaataaata aaataaaatg agacacttca    4140
gggatgtttc aacccttata caaaaccca aaaacaagtt tcctagcacc ctaccaacta    4200
aggtaccgag ctcagaattc gaatccaaaa attacggata tgaatatagg catatccgta   4260
tccgaattat ccgtttgaca gctagcaacg atttgtacaat tgcttcttta aaaaaggaag  4320
aaagaaagaa agaaaagaat caacatcagc gttaacaaac ggcccgtta cggcccaaac    4380
ggtcatatag agtaacggcg ttaagcgttg aaagactcct atcgaaatac gtaaccgcaa   4440
acgtgtcata gtcagatccc ctcttccttc accgcctcaa acacaaaaat aatcttctac   4500
agcctatata tacaacccc ccttctatct ctcctttctc acaattcatc atctttcttt    4560
ctctaccccc aatttttaga aatcctctct tctcctcttc attttcaagg taaatctctc   4620
tctctctctc tctctctgtt attccttgtt ttaattaggg atgtattatt gctagtttgt   4680
taatctgctt atcttatgta tgccttatgt gaatatcttt atcttgttca tctcatccgt   4740
ttagaagcta taaatttgtt gatttgactg tgtatctaca cgtggttatg tttatatcta   4800
atcagataga aatttcttca tattgttgcg tttgtgtgta ccaatccgaa atcgttgatt   4860
ttttcattt aatcgtgtag ctaattgtac gtatacatat ggatctacgt atcaattgtt   4920
catctgtttg tgtttgtatg tatacagatc tgaaaacatc acttctctca tctgattgtg   4980
ttgttacata catagatata gatctgttat atcatttttt ttattaattg tgtatatata   5040
tatgtcgata gatctggatt acatgattgt gattatttac atgattttgt tatttacgta   5100
tgtatatatg tagatctgga cttttttggag ttgttgactt gattgtattt gtgtgtgtat  5160
atgtgtgttc tgatcttgat atgttatgta tgtgcagcca aggctacggg cgatccacca   5220
tgtctccgga gaggagacca gttgagatta ggccagctac agcagctgat atggccgcgg   5280
tttgtgatat cgttaaccat tacattgaga cgtctacagt gaactttagg acagagccac   5340
aaacaccaca agagtggatt gatgatctag agaggttgca agatagatac ccttggttgg   5400
ttgctgaggt tgagggtgtt gtggctggta ttgcttacgc tgggcccctgg aaggctagga  5460
acgcttacga ttggacagtt gagagtactg tttacgtgtc acataggcat caaaggttgg   5520
gcctaggttc cacattgtac acacatttgc ttaagtctat gaggcgcaa ggttttaagt    5580
ctgtggttgc tgttataggc cttccaaacg atccatctgt taggttgcat gaggctttga   5640
gatacacagc ccgggtaca ttgcgcgcag ctggatacaa gcatggtgga tggcatgatg    5700
ttggttttttg gcaaagggat tttgagttgc cagctcctcc aaggccagtt aggccagtta   5760
cccagatctg agtcgaccga atgagttcca agatgggttg tgacgaagtt agttggttgt   5820
ttttatggaa ctttgtttaa gctagcttgt aatgtgaaa gaacgtgtgg ctttgtggtt    5880
tttaaatgtt ggtgaataaa gatgtttcct ttggattaac tagtattttt cctattggtt   5940
tcatggtttt agcacacaac attttaaata tgctgttaga tgatatgctg cctgctttat   6000
tatttactta cccctcacct tcagtttcaa agttgttgca atgactctgt gtagtttaag   6060
atcgagtgaa atagattttt gtctatattt attagggaga tttgatatgc taatggtaaa   6120
catggtttat gacagcgtac tttttggtt atggtgttga cgtttccttt taaacattat    6180
agtagcgtcc ttggtctgtg ttcattggtt gaacaaaggc acactcactt ggagatgccg   6240
tctccactga tatttgaaca aagaattcgt aatcatgtca tagctgtttc ctgtgtgaaa   6300
ttgttatccg ctcacaattc cacacaacat acgagccgga agcataaagt gtaaagcctg   6360
gggtgcctaa tgagtgagct aactcacatt aattgcgttg cgctcactgc ccgctttcca   6420
gtcgggaaac ctgtcgtgcc agatcgaccc aagtaccgcc acctaacaat tcgttcaagc   6480
cgagatcggc ttcccggcct agagtcgatc gacaagctcg agtttctcca taataatgtg   6540
tgagtagttc ccagataagg gaattagggt tcctatagg tttcgctcat gtgttgagca    6600
tataagaaac ccttagtatg tatttgtatt tgtaaaatac ttctatcaat aaaatttcta   6660
attcctaaaa ccaaaatcca gtactaaaat ccagatcccc cgaattaatt cggcgttaat   6720
tcagtacatt aaaaacgtcc gcaatgtgtt attaagttgt ctaag              6765

SEQ ID NO: 8           moltype = DNA   length = 19
FEATURE                Location/Qualifiers
misc_feature           1..19
                       note = Primer 15
source                 1..19
                       mol_type = other DNA
                       organism = synthetic construct
SEQUENCE: 8
cacagtcgac gccattgag                                                    19

SEQ ID NO: 9           moltype = DNA   length = 22
FEATURE                Location/Qualifiers
misc_feature           1..22
                       note = Primer 16
source                 1..22
                       mol_type = other DNA
                       organism = synthetic construct
SEQUENCE: 9
tcctaaaacc aaaatccagt ac                                                22

SEQ ID NO: 10          moltype = DNA   length = 20
FEATURE                Location/Qualifiers
misc_feature           1..20
                       note = Primer 707
source                 1..20
                       mol_type = other DNA
                       organism = synthetic construct
SEQUENCE: 10
```

```
gcaacaccca gtgacacaac                                            20

SEQ ID NO: 11           moltype = DNA   length = 21
FEATURE                 Location/Qualifiers
misc_feature            1..21
                        note = Primer 1170
source                  1..21
                        mol_type = other DNA
                        organism = synthetic construct
SEQUENCE: 11
aaatggctca tttaggagct g                                          21

SEQ ID NO: 12           moltype = DNA   length = 21
FEATURE                 Location/Qualifiers
misc_feature            1..21
                        note = Primer 656
source                  1..21
                        mol_type = other DNA
                        organism = synthetic construct
SEQUENCE: 12
tgaaattgag gttggctttc a                                          21

SEQ ID NO: 13           moltype = DNA   length = 22
FEATURE                 Location/Qualifiers
misc_feature            1..22
                        note = Primer 13
source                  1..22
                        mol_type = other DNA
                        organism = synthetic construct
SEQUENCE: 13
tatgttcaag aacattacca gc                                         22

SEQ ID NO: 14           moltype = DNA   length = 20
FEATURE                 Location/Qualifiers
misc_feature            1..20
                        note = Primer 1090
source                  1..20
                        mol_type = other DNA
                        organism = synthetic construct
SEQUENCE: 14
cgaatgctag agcagcttga                                            20

SEQ ID NO: 15           moltype = DNA   length = 20
FEATURE                 Location/Qualifiers
misc_feature            1..20
                        note = Probe 1091
source                  1..20
                        mol_type = other DNA
                        organism = synthetic construct
SEQUENCE: 15
tgaaggcggg aaacgacaat                                            20

SEQ ID NO: 16           moltype = DNA   length = 20
FEATURE                 Location/Qualifiers
misc_feature            1..20
                        note = Primer 716
source                  1..20
                        mol_type = other DNA
                        organism = synthetic construct
SEQUENCE: 16
cttttgcacg ttggtgaaga                                            20

SEQ ID NO: 17           moltype = DNA   length = 24
FEATURE                 Location/Qualifiers
misc_feature            1..24
                        note = Primer 1099
source                  1..24
                        mol_type = other DNA
                        organism = synthetic construct
SEQUENCE: 17
ggagaggaga ccagttgaga ttag                                       24

SEQ ID NO: 18           moltype = DNA   length = 21
FEATURE                 Location/Qualifiers
misc_feature            1..21
                        note = Primer 1546
source                  1..21
                        mol_type = other DNA
                        organism = synthetic construct
```

```
SEQUENCE: 18
gtgtggtagt tggcttgatg a                                          21

SEQ ID NO: 19          moltype = DNA  length = 20
FEATURE                Location/Qualifiers
misc_feature           1..20
                       note = Primer 1547
source                 1..20
                       mol_type = other DNA
                       organism = synthetic construct
SEQUENCE: 19
ctggaattac tgtgggttgc                                            20

SEQ ID NO: 20          moltype = DNA  length = 24
FEATURE                Location/Qualifiers
misc_feature           1..24
                       note = Probe 1548
source                 1..24
                       mol_type = other DNA
                       organism = synthetic construct
SEQUENCE: 20
tgcagaaatc cacagagtgc catg                                       24
```

TRANSGENIC SAFFLOWER EVENT STACK IND-1ØØØ3-4 X IND-1ØØ15-7 AND METHODS TO USE IT

RELATED APPLICATIONS

This application is a divisional of U.S. patent application Ser. No. 16/998,742, filed Aug. 20, 2020, the entire disclosure of which is incorporated herein by reference.

REFERENCE TO APPENDIX [CD ROM/SEQUENCE LISTING]

The instant application contains a Sequence Listing XML which has been submitted electronically in XML format and is hereby incorporated by reference in its entirety. Said XML copy, created on Oct. 12, 2022, is named "118991PD758D1_SEQ_LISTING.xml" and is 50,790 bytes in size.

FIELD OF THE INVENTION

The invention relates to the transgenic stacking of accumulated safflower through improvement IND-1ØØØ3-4 x IND-1ØØ15-7, and its plants, parts of it and seeds. These events allow the production of bovine chymosin in the seeds of safflower plants. This invention also relates to methods for detecting the presence of such safflower events in a biological sample and provides the nucleotide sequence specific to each event.

BACKGROUND OF THE INVENTION

Bovine chymosin is the enzyme used in the dairy industry for the coagulation of milk in cheese production. Originally, this enzyme was extracted from the stomachs of lactating calves. Due to increased demand, health problems and the high cost of production, it has been produced in recombinant form in bacteria and fungi using fermenters for almost 20 years. Today, more than 80% of the chymosin used in cheese production is of a recombinant origin.

The use of plants as bioreactors for the production of recombinant proteins has been widely documented. One of the advantages of the production of recombinant proteins in plants is the ease of scaling up production by increasing the cultivated area. By means of genetic engineering, safflower plants to accumulate chymosin in their seeds can be generated. This process of obtaining transgenic safflower with high expression of bovine chymosin in its seed requires the generation of transgenic events, as well as their molecular and phenotypic characterization, to identify and select the event that expresses the highest possible amount of active enzyme. In order to maximize the market potential of extracting chymosin by means of conventional equipment, more than one event can be combined.

The selection of each event has both development stages in the laboratory and field and/or greenhouse tests, where conditions are controlled. Analysis of events over several years, at multiple locations representing a variety of environmental conditions, is necessary to select the event that meets the phenotypic, genetic and marketing traits required. The selected event(s) must be very stable with regard to the level of expression and activity of the enzyme desired. These increases in expression shall not be related to losses in yield or grain quality. The present invention presents such commercially suitable events that give rise to new advantageous features in the chymosin-producing safflower seeds. These selected events can then be used to introduce said traits into other genotypes using breeding methods to produce different varieties containing the desired trait and adapted to specific growing conditions.

DETAILED DESCRIPTION OF THE INVENTION

The present invention provides chymosin-producing safflower plants containing the event stack IND-1ØØØ3-4 x IND-1ØØ15-7. These plants express the bovine enzyme chymosin in seeds allowing them to maintain their post-harvest catalytic activity while maintaining standard preservation conditions.

More specifically, the present invention refers to the safflower event stack designated as IND-1ØØØ3-4 x IND-1ØØ15-7, which has a representative seed deposited on 10 Jul. 2020 with the American Type Culture Collection (ATCC) with access number PTA-126769 and the descendants derived from it.

The present invention includes, additionally, safflower plants comprising the molecular stacking of the events IND-1ØØØ3-4 x IND-1ØØ15-7 represented by SEQ ID NO: 1 and SEQ ID NO: 2.

The transgenic inserts present in the molecular stack of the invention and in the registered seed comprise the following genes: one single copy of the selection marker gene pat and a single copy of the gene that codes for the enzyme chymosin cym, with a copy of each insert present in the molecular stack of events IND-1ØØØ3-4 x IND-1ØØ15-7. The pat gene derived from *Streptomyces viridochromogeness* codes the protein PAT (Phosphinothricin Acetyl Transferase). The cym gene derives from *Bos taurus* sp. bovine and codes for the chymosin enzyme, which possesses aspartic protease activity with the ability to coagulate milk. Regulation of the genes of interest may be directed by various promoter sequences that have different levels of expression, sensitivity and tissue specificity. Subject-matter experts know that any nucleic acid promoter or terminator can be used to direct or regulate the expression of the gene of interest without altering the essence of the invention. In particular, the event developed in this invention contains the ubiquitin promoter (prUBI) and the terminator TerUBI for the gene pat, which confers resistance to the glufosinate-ammonium herbicide. On the other hand, the event contains the phaseolin promoter (prPHA) and the terminator TerPHA to regulate the expression of the codifying region of cym (FIG. 1) in each of its inserts.

Other aspects of the invention comprise the progeny of safflower plants, seeds, and/or regenerative parts of plants and seeds and progeny comprising the molecular stacking of safflower events IND-1ØØØ3-4 x IND-1ØØ15-7, as well as food and feed derived therefrom. The invention also includes parts of plants comprising the molecular stacking of safflower events IND-1ØØØ3-4 x IND-1ØØ15-7, including, but not limited to, pollen, eggs, flowers, buds, roots, leaves, nuclei of vegetative cells, and other plant cells comprising the molecular stack of safflower events IND-1ØØØ3-4 x IND-1ØØ15-7. The invention further relates to safflower plants comprising the molecular stacking of safflower events IND-1ØØØ3-4 x IND-1ØØ15-7 which express the chymosin enzyme in seeds.

This invention relates in part to the cultivation of enzyme-producing plants. In addition, it includes the novel molecular stacking of two transformation events in safflower plants comprising polynucleotides, as described herein, inserted at specific points within the safflower genome that confer particular genetic and phenotypic traits.

In some forms of realization, such events/polynucleotides may be "stacked" with other traits including, for example, agronomic, quality, and herbicide and/or insect tolerance traits. The present invention includes plants that have an individual event derived from stacking by crossing inserts with similar traits, as described herein.

Additional traits can be stacked in the plant genome or at the same locus as the molecular stack of safflower events IND-10003-4 x IND-10015-7, for example, through plant breeding, retransformation of the transgenic plant containing the molecular stack of safflower events IND-10003-4 x IND-10015-7, or addition of new traits thru the homologous recombination directed integration.

In a form of realization, the present invention comprises two genomic points of safflower. In some forms of realization, the directed point comprises a heterologous nucleic acid. Safflower genomic points are located between the flanking sequences established in SEQ ID NO: 3: (right junction region of IND-10003-4), SEQ ID NO 4 (left junction region of IND-10003-4), SEQ ID NO: 5: (right junction region of IND-10015-7), SEQ ID NO: 6 (left junction region of IND-10015-7).

In a form of realization, the present invention comprises a method for the production of transgenic safflower plants, involving inserting heterologous nucleic acids at specific positions in the genome.

In particular, the method comprises transforming a cell or a cellular culture in a stable form with the sequences ADN SEQ ID NO 7: insert and regenerate the cell giving rise to an entire plant.

The transformation of such a plant cell can be carried out through various techniques, whether physical, viral or chemical. Among them: bio-ballistics, electroporation, transformation by bacteria, or the combination of some of them. All of these techniques are well known to the knowledgeable person.

The invention further presents a microorganism comprising a nucleic acid molecule with a nucleotide sequence selected from the group SEQ ID NO: 1 and SEQ ID NO: 2.

In particular, this invention uses *Agrobacterium tumefaciens* transformed with the DNA molecule from SEQ ID NO 7, more precisely transformed with plasmid pSBS2165 (FIG. 1).

In addition, this invention provides tests for detecting the presence of the molecular stack of safflower events herein in a safflower sample. The tests may be based on the DNA sequence of the recombinant construct, inserted into the safflower genome, and on the genomic sequences flanking the insertion points. Kits and conditions that are useful in testing are also provided.

Therefore, the present invention relates in part to the cloning and analysis of the DNA sequences of all or part of the inserts and flanking regions (in transgenic safflower lines). These sequences are unique. On the basis of these inserts and the flanking (and bonding) sequences, it is possible to generate event-specific primers. The PCR technique showed that these events may be identified by analysis of the amplicons generated with these event-specific primer sets. Therefore, these and related procedures can be used to uniquely identify safflower lines comprising the events of the present invention.

This invention also relates in part to PCR tests. These include real-time qPCR or end-time PCR among others, for the detection of molecular stacking of safflower events IND-10003-4 x IND-10015-7, or each of them separately IND-10003-4 and IND-10015-7, amplicons and fragments thereof.

The invention also presents DNA molecules comprising a sufficient length of the sequence of contiguous nucleotides of SEQ ID NO: 14 and 20 so that it works as a DNA probe that hybridizes, under rigorous hybridization conditions, to a DNA molecule comprising a sequence of nucleotides selected from the group consisting of SEQ ID NO: 1 and SEQ ID NO: 2, and that does not hybridize under rigorous hybridization conditions to a DNA molecule not comprising a sequence of nucleotides selected from the group consisting of SEQ ID NO: 1 and SEQ ID NO: 2.

In some cases, the probes used may be marked with molecules that emit a detectable signal. An example of such molecules is fluorochromes. That is to say, oligonucleotides that present fluorochromes at both ends and have a complementary sequence to part of the DNA fragment to be amplified. Among them are FAM, TET, HEX, JOE, CAL Fluor®, Quasar®, and Pulsar® dyes, among other.

The invention further discloses a pair of DNA molecules consisting of a first DNA molecule and a second DNA molecule different from the first DNA molecule, where each of the first and second DNA molecules comprises a sufficient stretch of contiguous nucleotides of SEQ ID NO: 1 and SEQ ID NO: 2: to function as DNA probes if used together in an amplification reaction with DNA derived from the molecular stacking of safflower events IND-10003-4 x IND-10015-7, to produce two diagnostic DNA amplicons of the molecular stack of transgenic safflower events IND-10003-4 x IND-10015-7 in one sample.

The invention further describes a method for detecting the presence of DNA obtained from the molecular stacking of safflower events IND-10003-4 x IND-10015-7 in one sample. The method involves checking the sample against the DNA molecules used as probe and primers, subjecting them to rigorous hybridization conditions, and detecting hybridization of the DNA probe to the DNA in the amplified sample, with the use of specific primers, where such hybridizations indicate the presence of DNA derived from the transgenic safflower event IND-10003-4 x IND-10015-7 in the sample.

The invention also presents a method for detecting the presence of DNA molecules obtained from the molecular stacking of safflower events IND-10003-4 x IND-10015-7, in one sample, by matching the DNA preparation derived from it with a pair of oligonucleotides used as primers to perform an amplification reaction sufficient to produce DNA amplicons comprising selected sequences from the group consisting of SEQ ID NO: 1 and SEQ ID NO: 2 and, by detecting the presence of DNA amplicons in the reaction, where the presence of DNA amplicons in the reaction indicates the presence of a DNA molecule derived from the molecular stacking of safflower events IND-10003-4 x IND-10015-7 in the sample.

The invention further presents a DNA detection kit comprising at least one DNA molecule with a sufficient amount of contiguous nucleotides of SEQ ID NO: 1 and SEQ ID NO: 2 to work as specific DNA primer or probe to detect the presence of DNA derived from the molecular stacking of safflower events IND-10003-4 x IND-10015-7, where the DNA detection is diagnostic of the presence of the molecular stack of safflower events IND-10003-4 x IND-10015-7 in one sample.

The invention further presents a safflower plant, seed, cell or part of such a plant comprising nucleic acid molecules having sequences SEQ ID NO: 1 and SEQ ID NO: 2. The invention further presents a safflower plant, seed, cell or part of a plant expressing chymosin. The invention further presents a safflower plant, seed, cell or part of a plant, the genome of which produces an amplicon comprising DNA molecules having sequences SEQ ID NO: 1 and SEQ ID NO: 2 when analyzed by a DNA amplification method.

The invention further presents a safflower plant or seed, where the safflower plant or seed is generated from the molecular stacking of safflower events IND-1ØØØ3-4 x IND-1ØØ15-7, or each of them separately IND-1ØØØ3-4 and IND-1ØØ15-7, o is a hybrid or heterozygous that has at least one parent derived from the transgenic safflower event IND-1ØØØ3-4 x IND-1ØØ15-7, c IND-1ØØØ3-4 and IND-1ØØ15-7.

The invention further presents non-living plant material comprising recombinant DNA molecules having sequences SEQ ID NO: 1 and SEQ ID NO: 2.

The invention further presents a consumer product produced as a consequence of the molecular stacking of safflower events IND-1ØØØ3-4 x IND-1ØØ15-7, and comprising nucleic acid molecules selected from the group consisting of SEQ ID NO: 1 and SEQ ID NO: 2, where the detection of a nucleotide sequence in a sample derived from a consumer product is decisive for the consumer product to be derived from the molecular stacking of safflower events IND-1ØØØ3-4 x IND-1ØØ15-7, or each of them separately IND-1ØØØ3-4 and IND-1ØØ15-7.

The invention further presents a method for producing a consumer product by obtaining a safflower plant or part thereof, comprising the molecular stacking of safflower events IND-1ØØØ3-4 x IND-1ØØ15-7 and for producing a consumer product from a safflower plant or part thereof.

The invention presents a method for producing a safflower plant that produces the enzyme chymosin by crossing a plant with the molecular stacking of safflower events IND-1ØØØ3-4 x IND-1ØØ15-7, or each of them separately IND-1ØØØ3-4 and IND-1ØØ15-7. The progeny resulting from the use of these methods can be varieties or hybrids, homozygotes or heterozygotes for IND-1ØØØ3-4 and IND-1ØØ15-7. Plants can be self-fertilized or crossed-fertilized. Plants with the events can be self-fertilized to produce inbred, genetically uniform, homozygous lines for IND-1ØØØ3-4 and IND-1ØØ15-7. Alternatively, the progeny can be cross-fertilized to produce varieties or hybrids. The seed of the progeny thus produced contains the events IND-1ØØØ3-4 and IND-1ØØ15-7 and may be used to obtain chymosin. The plants of the progeny can be analyzed using diagnostic methods or molecular markers that allow the identification of events IND-1ØØØ3-4 and IND-1ØØ15-7. In addition, these plants can be treated with glufosinate herbicide for selection.

BRIEF DESCRIPTION OF THE DRAWINGS

FIGS. 7A to 7D: T-DNA flanking sequences in events IND-1ØØØ3-4 and IND-1ØØ15-7. A) and B) Flanking sequences neighboring the left border (LB) and right border (RB), respectively, of event IND-1ØØ15-7. C) and D) Flanking sequences neighboring the left border (LB) and right border (RB), respectively, of event IND-1ØØØ3-4. The bases within the border correspond to the safflower genome and the bases outside of the border correspond to the T-DNA of each insert.

BRIEF DESCRIPTION OF THE SEQUENCES

Figure 1:
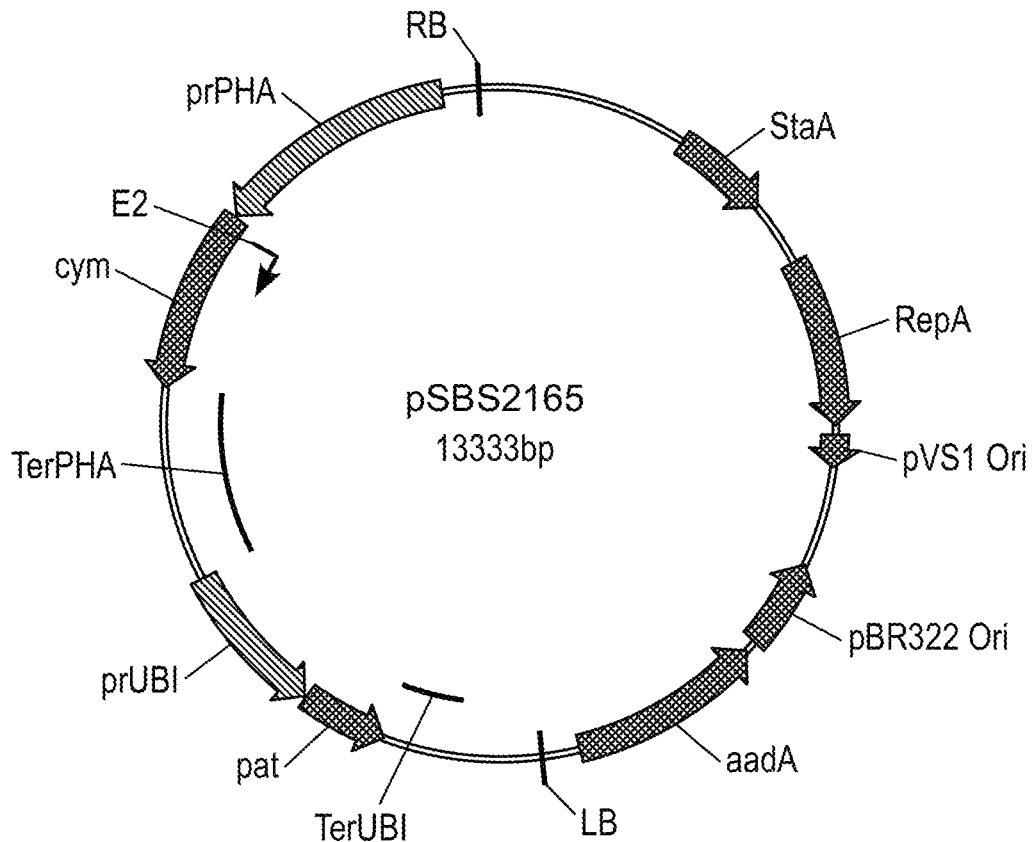
FIG. 1: Transformation vector diagram pSBS2165.

SEQ ID NO: 1 Representative sequence of the event IND-1ØØØ3-4. This sequence includes the genomic region 5' of the joint point, the complete insert and the genomic region 3' of the joint point
SEQ ID NO: 2 Representative sequence of the event IND-1ØØ15-7. This sequence includes the genomic region 5' of the joint point, the complete insert and the genomic region 3' of the joint point
SEQ ID NO: 3 Right splicing of the event IND-1ØØØ3-4
SEQ ID NO: 4 Left splicing of the event IND-1ØØØ3-4
SEQ ID NO: 5 Right splicing of the event IND-1ØØ15-7
SEQ ID NO: 6 Left splicing of the event IND-1ØØ15-7
SEQ ID NO: 7. Complete insert sequence
SEQ ID NO: 8 primer 15
SEQ ID NO: 9 primer 16
SEQ ID NO: 10 primer 707
SEQ ID NO: 11 primer 1170
SEQ ID NO: 12 primer 656
SEQ ID NO: 13 primer 13
SEQ ID NO: 14 primer 1090
SEQ ID NO: 15 probe 1091
SEQ ID NO: 16 primer 716
SEQ ID NO: 17 primer 1099
SEQ ID NO: 18 primer 1546
SEQ ID NO: 19 primer 1547
SEQ ID NO: 20 probe 1548

DETAILED DESCRIPTION

The following examples illustrate procedures for implementing the invention and to demonstrate certain preferred forms of implementation of the invention. Such examples should not be interpreted as restrictive. Technical experts should appreciate that the techniques disclosed in the following examples represent specific methods used to illustrate preferred modes of practice. However, in view of the present disclosure, technical experts should appreciate that various changes can be made to such specific forms of implementation while obtaining similar or like results without departing from the spirit and scope of the invention.

EXAMPLES

Example 1: Construction of Plasmid pSBS2165

Plasmid pSBS2165, which would later be used for the processing of safflower plants, is derived from the family of pPZP binary plasmids. In particular, it is based on the pPZP200 series.

The transgenic insert and the expression cassette present at the events IND-1ØØØ3-4 and IND-1ØØ15-7 includes the ubiquitin promoter (prUBI) and the terminator TerUBI for the pat marker gene. Additionally, it includes the promoter of the gene pha of *Phaseolus vulgaris* and the terminator TerPHA for the gene cym.

The resulting plasmid pSBS2165 is shown in FIG. 1.

Example 2: Transformation of Safflower Plants and Selection of the Molecular Stack of Safflower Events IND-1ØØØ3-4 x IND-1ØØ15-7

The initial step in a transformation test is the preparation of bacterial suspensions of a strain of *Agrobacterium tumefaciens*, which carries the genes of interest and selection accompanied by the molecular sequences necessary for their expression in plants. These bacterial cultures are used as biological vectors for the transformation of plant cells and for the subsequent regeneration of transforming plants. For this, it is a requirement to maintain fresh colonies of *A. tumefaciens* at 28° C. on Petri dishes with semi-solid culture media added with selective agents (antibiotics for bacterial selection). From these colonies, bacterial cultures in liquid suspension are initiated for the infection of the transformation target explants.

The protocol developed in the processing and tissue culture laboratory defines as starting material to be used in processing trials the Centennial cultivar of Carthamus tinctorius, sections of cotyledon tissue obtained from pre-germinated seeds in sterility (5-6 days post-germination in darkness). These materials constitute totipotent explants, capable of de-differentiating and then regenerating safflower transgenic shoots under selective in vitro conditions. Once inoculated with *A. tumefaciens*, these explants constitute the starting material for in vitro regeneration of de novo transgenic plants.

The activities involved are described in stages below:
Surface Disinfection of Seeds and Obtaining Explants The starting point in the transformation process is the surface disinfection of the safflower cv Centennial seeds. This process consists of washing the seeds in a diluted chlorine [11 g $Cl_2$/L] and detergent solution for 60 minutes, ending with three washes with sterile distilled water. The seeds are then left to incubate for 16 hours in an antibiotic and antifungal disinfectant solution (timentin [400 mg/L] and nystatin [125 mg/L]). Once this time has elapsed, the seeds are peeled and sown in a germination culture containing: 0.5×MS Medium, 10 g/L Sucrose and 8 g/L Agar, pH 5.8 in a Petri dish of 90 mm×25 mm for 5 days.

Transformation Procedure

The germinated seeds are selected and placed in a Petri dish with 5 mL of inoculation medium containing: 0.2×MS Medium, Glucose 10 g/L, Acetosyringone 100 uM, pH: 5.8.

Using a #11-scalpel blade, cuts were made in the cotyledons obtaining thin pieces of 1 mm width, which will be the actual transformation explants. These explants are then brought into contact with a suspension of *A. tumefaciens* and incubated in agitation for 30 minutes. Subsequently, the period of indirect co-cultivation of the explants in darkness begins for 5-6 days at 24° C. The co-cultivation medium contains 0.2×MS Medium, Glucose 10 g/L, Acetosyringone 100 uM and Agar 12 g/L pH: 5.8 in a 90 mm×25 mm Petri dish.

Selection and Regeneration of Transformed Explants

After co-culture, the explants are transferred to callus-inducing medium, whose composition is 1×MS Medium, 30 g/L Sacarose, 2 g/L Gelzan, TDZ 0.2 mg/L, ANA 0.5 mg/L, Timentin 200 mg/L, and Glufosinate ammonium 3 mg/L, pH 5.8 in a 90 mm×25 mm Petri dish. The material must be kept for 30 days in darkness at 24° C.

Then, the generated callus must be sub-cultivated in sprout inducing medium with a composition of: 1×MS medium, 30 g/L Sacarose, 2 g/L Gelzan, Kinentin 0.5 mg/L, 2 iP 1 mg/L, Timentin 200 mg/L, Cefotaxime 200 mg/L, Glufosinate ammonium 3 mg/L and pH 5.8 in a 90 mm×25 mm. Petri dish. The material must be maintained for 3 months by performing periodic sub-cultures every 21 days. At this stage, the photoperiod is 16:8 hours light/darkness at 24° C.

The obtained neoformations are replanted into a sprouts development medium containing 1×MS medium, 30 g/L Sacarose, 2 g/L Gelzan, BAP 0.1 mg/L, IBA 0.1 mg/L, Timentin 200 mg/L, Cefotaxime 200 mg/L, Glufosinate ammonium 3 mg/L and pH: 5.8 in a 90 mm×25 mm Petri dish. The material is kept at a photoperiod of 16:8 hours of light/darkness at 24° C.

Sprouts that reach a height greater than 1 cm are replanted into an elongation medium, which differs from the sprouting medium in that it does not carry growth regulators or selector agent and, the gelling agent is agar at a final concentration of 6 g/L. For this period, the necessary photoperiod is 10/14 hours of light/darkness at 24° C. As in the previous instances, the material must be sub-cultivated every 21 days in 400 cm$^3$ glass containers.

Ex Vitro Hardening and Rooting

When the shoots generated in vitro reach a height of approximately 6-7 cm, they are hardened off. For this process, it is necessary to autoclave-sterilize the mixed substrate at 121° C. for 80 minutes.

At the time of hardening, the film covering the jars is removed by extracting the elongated shoots, which are washed at their basal end under running water. Immediately a perpendicular cut is made on the stem, a few millimeters above the base, adding a rooting solution (Dip'n&grow) for 1 minute. After this time, the sprouts are sown in 180 cm$^3$ containers perforated at its base, containing the sterile mixed substrate. The containers containing the sprouts are placed inside transparent plastic pots of approximately 1.2 L with 20-25 cm$^3$ water and are covered with 2 layers of film to keep the humidity inside. The material is kept in chambers under controlled conditions: photoperiod of 10-14 hours of light/darkness, 24° C. temperature and light intensity of 9500-10500 lux.

Acclimatization

Those plants that successfully overcome the rooting period are transplanted into larger pots using the same sterile mixed substrate that was used in the hardening. In this instance, the specimens are generally in a position to be molecularly characterized by PCR. For this purpose, leaf tissue samples are taken in 2 mL microtubes. After the molecular analysis, the transgenic events can be identified, that is, those specimens that are positive for the transgene of interest.

Such transgenic events will receive a unique traceability ID and must be maintained under controlled conditions until full harvest of $T_1$ seeds.

Pre-Selection of Events

Eighty-two transgenic safflower events derived from different *agrobacterium*-mediated transformation trials and different molecular expression strategies were evaluated. For all three strategies, the centennial safflower variety was used in the transformation experiments. T1 seeds were obtained for all independent events. The first multiplication of the transformed plants was carried out in a greenhouse and T1 individuals derived from each event were sampled for a Mendelian segregation test by PCR determination. After these analyses, the non-segregated Mendelian lines were discarded. Lines derived from self-pollinations of individuals from selected events (Mendelian segregation 3:1 in T1) were chosen. Phenotypes with different traits were identified during the growing season, scored and discarded. In order to identify homozygous lines, the plants were sampled for PCR analysis during the vegetative stages. The increase of seeds (T3 seeds) of homozygous and null lines was carried out in a greenhouse. Additionally, the level of expression of the cym gene on homozygous lines was evaluated by transcriptional expression analysis. For this purpose, the transcripts corresponding to T2 achenes from transgenic T1 plant chapters obtained with three different molecular expression strategies were detected and quantified. In most cases, one chapter per plant and three plants per transgenic event (i.e., three chapters per event) were taken. As a negative expression control, Centennial plant achenes were taken. Samples were taken from mature achenes and RNA was extracted from seed pools from the same chapter (using the RNeasy Plant Mini Kit QIAGEN commercial kit). The integrity of the purified RNA is assessed by running 5 μL of each sample in an agarose gel at 1% in TAE buffer. Once the integrity of these was corroborated, the quantification was carried out using the Quant-iT™ RiboGreen® RNA Assay kit. Then, 2 μg RNA from each sample was treated with DNase I to remove possible traces of genomic DNA (gDNA) that may have remained during the extraction. In order to corroborate the DNase treatment, a final time PCR was performed using specific oligonucleotides for the FAD2-1 gene. A PCR reaction for an endogenous safflower gene was then performed on the RNA samples to rule out DNA contamination. Finally, using Oligo dT, the reverse transcription was performed. The synthesized cDNAs were diluted and used for real-time PCR analysis of the expression level of the gene of interest, using appropriate controls. The expression of the gene of interest was analyzed using FAD2-1 as a standardizing gene. Of the three molecular expression strategies evaluated, one yielded results that allowed us to rule out the events obtained due to null chymosin expression levels.

To continue the selection, 22 transgenic safflower events belonging to two different molecular strategies were evaluated under field conditions. Evaluations were made of seed quantity and quality, as well as the level of activity of the chymosin recovered from the seeds.

Using as a last selection criterion the level of activity of recovered chymosin, two homozygous lines belonging to 2 different events were selected. Both events derive from the same transformation test with the same molecular expression strategy.

Selection of Events IND-10003-4 and IND-10015-7 and Stacking to Allow Purification of Chymosin with Standard Equipment Among the events obtained in the first stages of the project, a preliminary selection was made, discarding those events that showed agricultural penalties or lack of expression and activity of chymosin.

From these considerations, two events were selected: the transgenic safflower event IND-10003-4 and the transgenic safflower event IND-10015-7.

As of 2008, IND-10003-4 and IND-10015-7 safflower transgenic events began to be evaluated, mainly with regard to the expression and activity of chymosin in seeds, stability and other useful parameters.

To quantify the level of chymosin expression in the seeds, the coagulating capacity of milk in extracts from the different grain samples was analyzed. This clotting activity is expressed as IMCU/mL (International Milk Clotting Units per milliliter of tested solution) and the chymosin mass per gram of safflower seed.

Materials and Methods

The safflower grains were macerated in a mortar (0.1 gr/mL of extraction buffer $NaH_2PO_4$ 50 mM, NaCl 1.2 M, pH=6) at room temperature. After centrifugation at 11,000×g for 20 minutes, the supernatants obtained were used to measure the clotting activity.

Chymosin activity was measured following the method recommended by the International Dairy Federation (IDF 157, ISO 11815). Svelty milk powder (low heat, low fat) dissolved in a $CaCl_2$) 4.5 mM (0.11 gr/mL) solution was used as a substrate. An aliquot (500 μL) of the seed extract or a universal standard solution (CHR Hansen, 5 mg/mL in sodium acetate 73.5 mM, pH=5.5) was added to 25 mL of substrate preheated at 32° C. and incubated at this temperature in a continuously rotating water bath. The clotting time (in seconds) was used to calculate the activity using the formula: $t_{ref} \times c_{ref} \times a_{ref}/t_m$. Where:

$t_{ref}$=pattern clotting time, $c_{ref}$=universal standard concentration (in g/mL), $a_{ref}$=standard original activity (in IMCU: International Milk Clotting Units/gr) and $t_m$=sample clotting time.

In order to transform the values of the enzymatic activity into chymosin mass, the value of the intrinsic clotting activity of chymosin expressed in safflower seeds was used (SPC—Safflower Produced Chymosin). To this end, the specific activity (IMCU/mg) in 13 pure SPC preparations and the total protein concentration were determined. With these results, the specific activity (Ae) of SPC (109 IMCU/mg) was calculated.

Seed extracts from non-transgenic safflower showed no clotting activity (data not shown).

Results

The methodology used to obtain these transgenic events causes random insertion anywhere in the plant's genome. Accordingly, it is extremely unlikely that the inserts of different events are in the same place on the genome. The different location would make it possible for the conventional crossing of plants with two different insertion events to result in a stack that expresses greater clotting activity in its seeds than either of its parents. To this end, progress was made with the transgenic safflower event IND-10003-4 and the transgenic safflower event IND-10015-7.

In order to analyze the result of this process, the chymosin activity in seeds of the transgenic safflower event IND-10003-4, the transgenic safflower event IND-10015-7 and the product of its stacking, molecular stacking of safflower events IND-10003-4 x IND-10015-7 was measured again.

Figure 2:
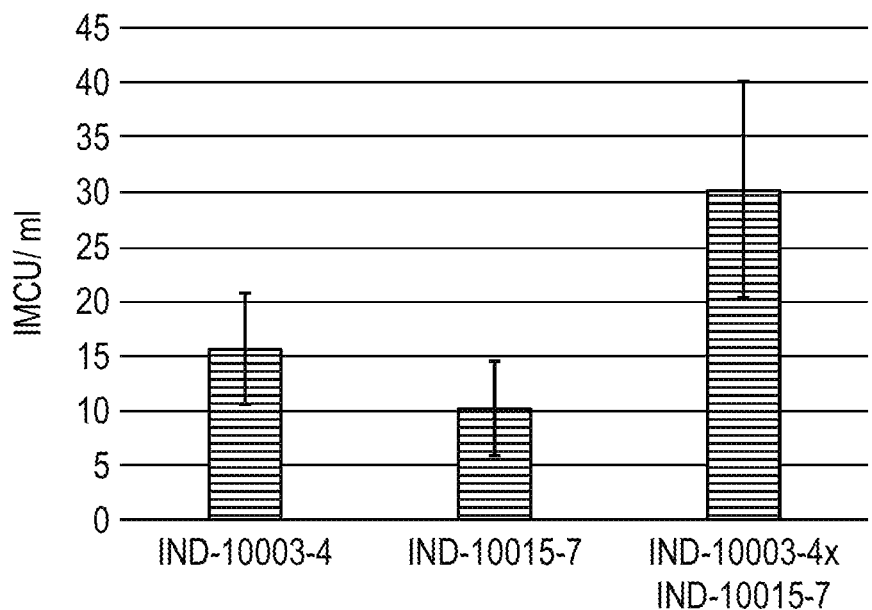
FIG. 2: Clotting activity. The ability to coagulate milk from seed extracts was measured from the transgenic safflower event IND-1ØØØ3-4, from the transgenic safflower event IND-1ØØ15-7, and from the stacking IND-1ØØØ3-4 x IND-1ØØ15-7.
Figure 3:
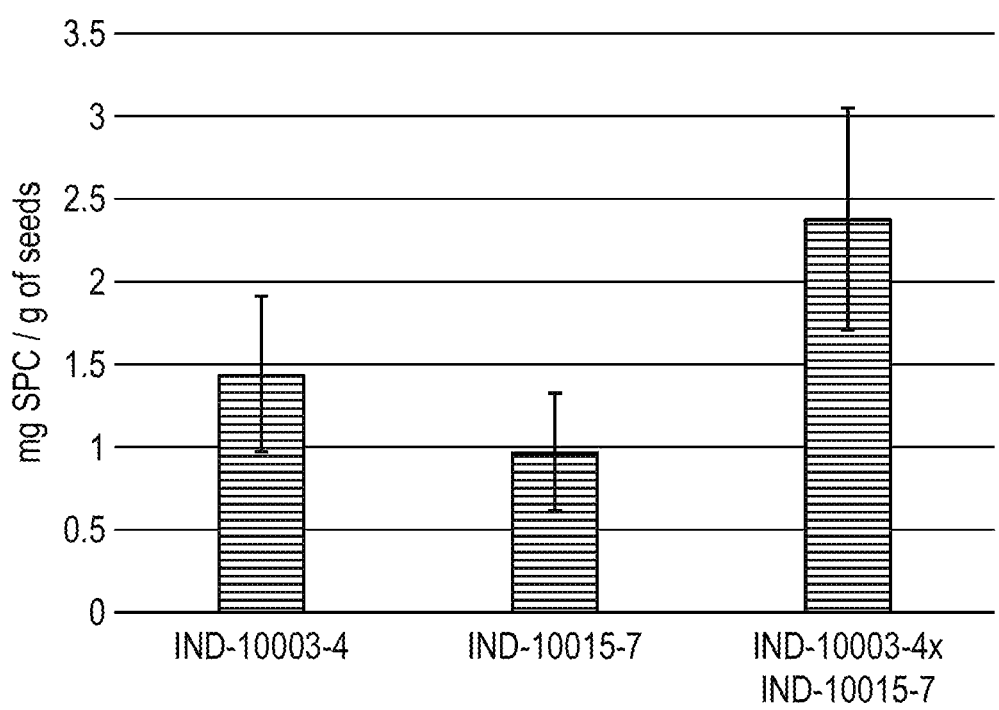
FIG. 3: Content of chymosin. The bovine chymosin content in seeds was determined from the transgenic safflower event IND-1ØØØ3-4, from the transgenic safflower event IND-1ØØ15-7, and from the product of its stacking (IND-1ØØØ3-4 x IND-1ØØ15-7).

The result of the stacking of the two transgenic safflower events (IND-10003-4 x IND-10015-7) contains in its seed more clotting activity and more chymosin than its parental lines (FIGS. 2 and 3). These results confirm that the stacking yielded a more efficient and profitable variety of transgenic safflower for the purification of chymosin, a criterion used for the selection of the transgenic safflower IND-10003-4 x IND-10015-7.

Example 3: Characterization of the DNA Sequences of the Safflower Event IND-10003-4 x IND-10015-7

The molecular characterization of transgenic safflower plants with both insertion events, belonging to the molecular stack of safflower events IND-10003-4 x IND-10015-7, obtained by crossing IND-10003-4 and IND-10015-7, was carried out using Southern blot and molecular biology techniques involving the amplification of specific DNA fragments by polymerase chain reaction and, in some cases, their subsequent sequencing.

Analysis of the Number of Copies of Coding Regions of Interest

By means of Southern blot, the number of copies present both in the separate events and in the product of their crossing was determined, thus determining the presence of only one copy of the cym gene of interest, and another in the same locus of the pat companion, using probes that hybridize with these particular regions.

Figure 4A:
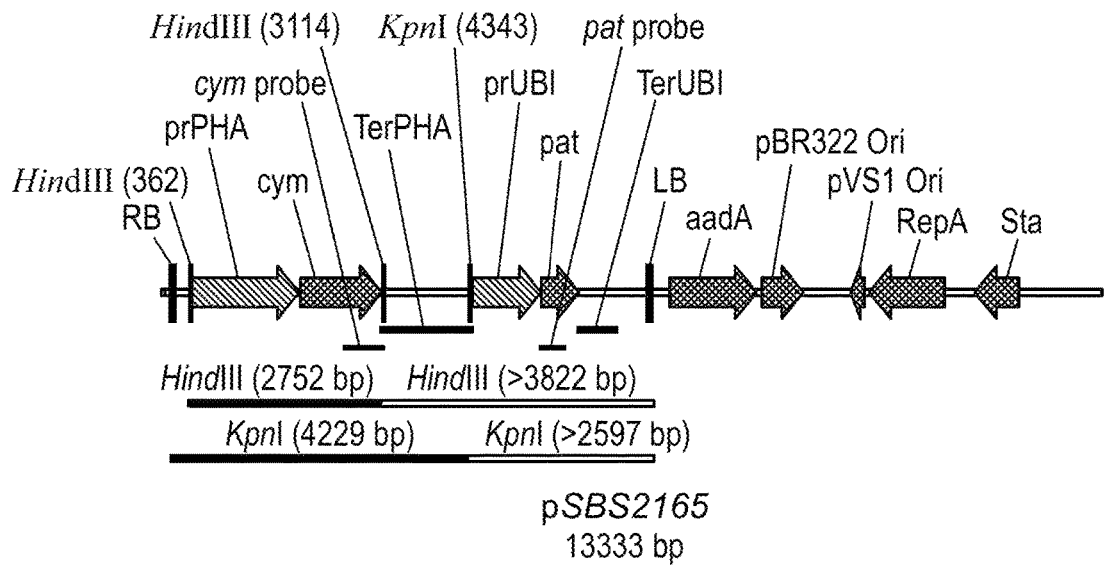
FIGS. 4A and 4B: Sequence diagrams involved in the transformation process. A) Linear plasmid map pSBS2165. B) Diagram of expected T-DNA insertion. In both diagrams, restriction points and probes used for event analysis are highlighted by Southern Blot (cym and pat, horizontal lines indicated) and the flanks of the joint point corresponding to the safflower genome (boxes with vertical line shading). The horizontal solid lines HindIII and KpnI indicate the fragments obtained by digesting genomic DNA with HindIII or with KpnI, and hybridizing with a cym probe. The horizontal non-solid lines HindIII and KpnI indicate the fragments obtained by digesting genomic DNA with HindIII or with KpnI, and hybridizing with a pat probe.
Figure 4B:
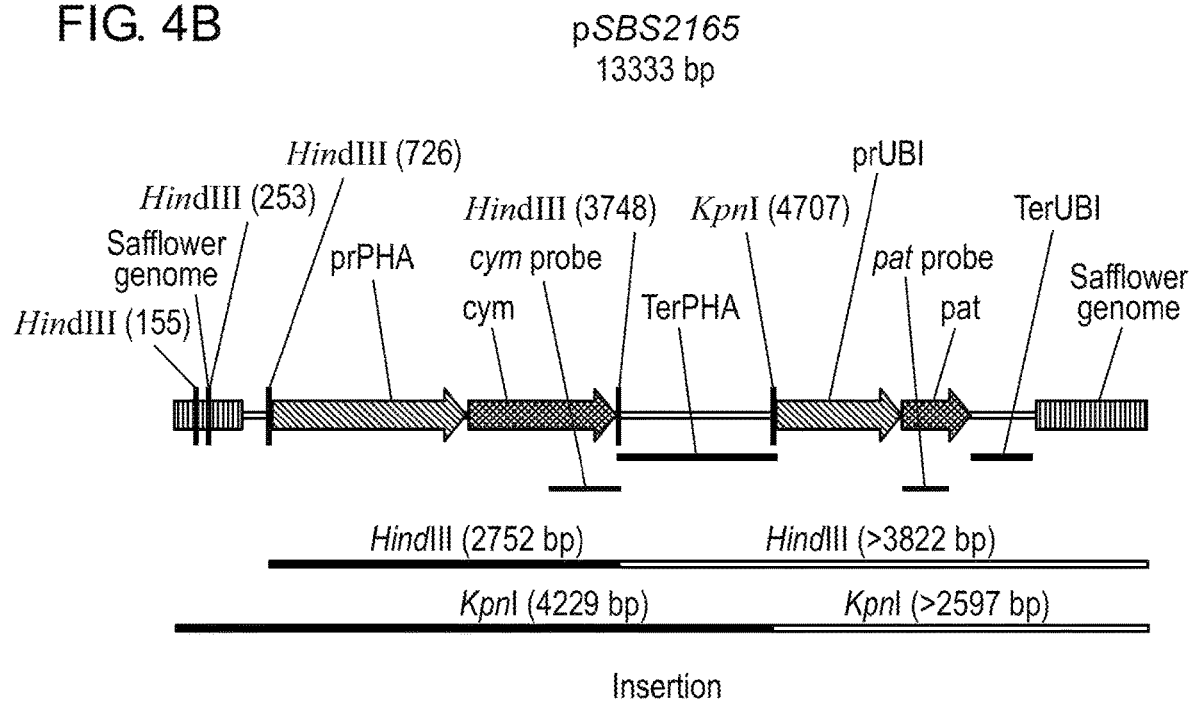

The digestion of the genomic DNA prior to the electrophoretic run was done with the HindIII and KpnI enzymes. There are two restriction sites of HindIII enzyme in the T-DNA of the construct used to originate the transgenic events (FIG. 4).

The cym hybridizing probe detected a single band of the expected size (2752 bp) in the streets corresponding to the genomes of IND-10003-4, IND-10015-7 and IND-10003-4 x IND-10015-7 digested with HindIII. This would indicate the absence of major re-arrangements in the region comprising the cym coding region and the promoter that digests its expression, prPHA. On the other hand, when the genomic DNA was digested with KpnI, a band could be observed at each of the insertion events, IND-10003-4 and IND-10015-7, of a size greater than 4229 bp, originated from the only cutting site present in the T-DNA and the closest site present in the plant's genome. Both bands are sufficiently different in size from each other and, as expected, could also be detected in the event IND-10003-4 x IND-10015-7. No bands were detected on the streets corresponding to the Centennial non-GM parent.

As for the pat probe, when digesting genomic DNA with HindIII, a band was detected for each event IND-10003-4 and IND-10015-7, both of a size greater than 3822 bp of the expected minimum. These same bands were detected in the event originated by crossing IND-10003-4 x IND-10015-7. A similar result was obtained by digesting genomic DNA with KpnI.

Detection of Non-T-DNA Sequences

The verification of the absence of undesired plasmid sequences in transgenic events was performed by PCR with different combinations of oligonucleotides. These oligonucleotides were designed to amplify segments covering the entire plasmid region pSBS2165 outside the T-DNA, that is, that hybridize with the region that is not desired.

Figure 5A:
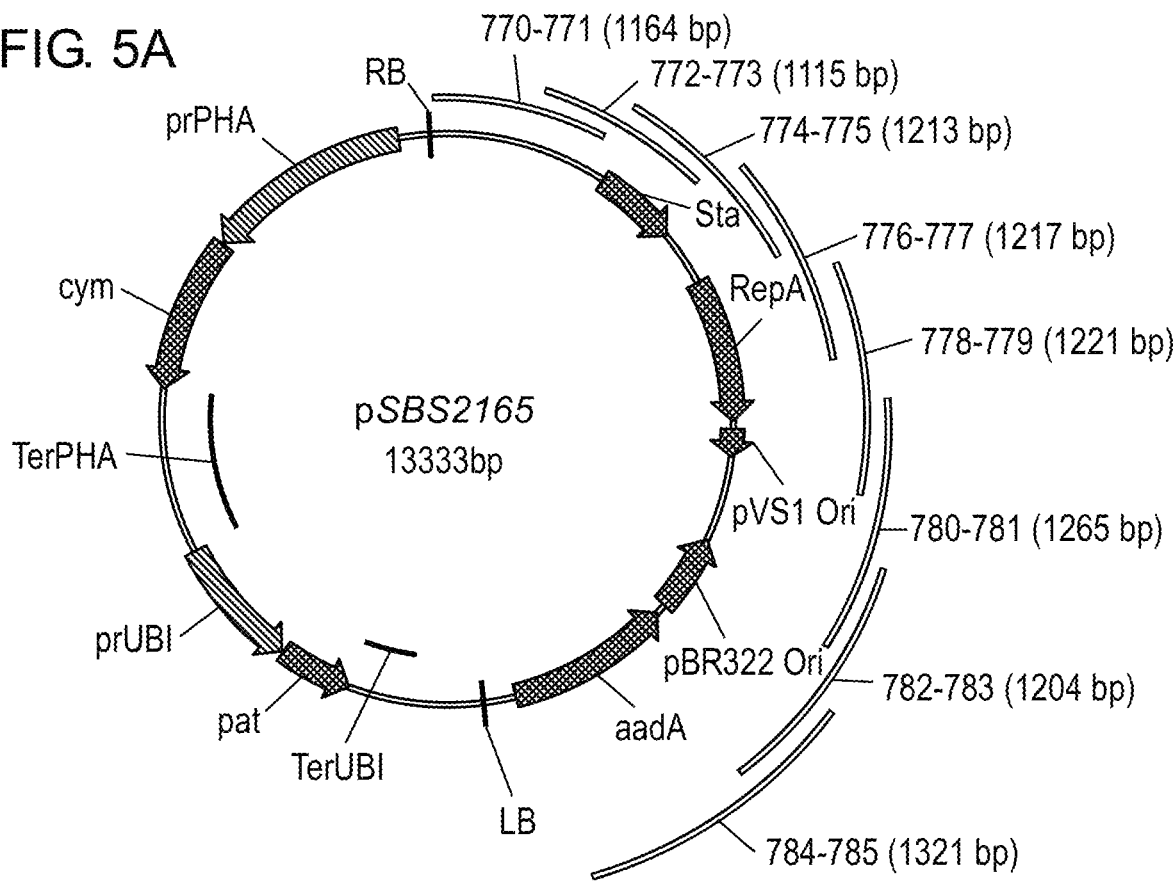
FIGS. 5A and 5B: Diagram of the amplified segments for the analysis of the presence of non-T-DNA plasmid regions in events IND-1ØØØ3-4 and IND-1ØØ15-7. A) Overlapping fragments, non-solid lines indicate segments greater than 1000 bp amplified with each set of initiating oligonucleotides. Each segment indicates the initiating oligonucleotides used and the size of the amplicons in parentheses. B) Non-overlapping fragments, green lines indicate segments between 400 and 600 bp amplified with each set of initiating oligonucleotides. In each segment, the initiating oligonucleotides used and the size of the amplicons are indicated in parentheses.
Figure 5B:
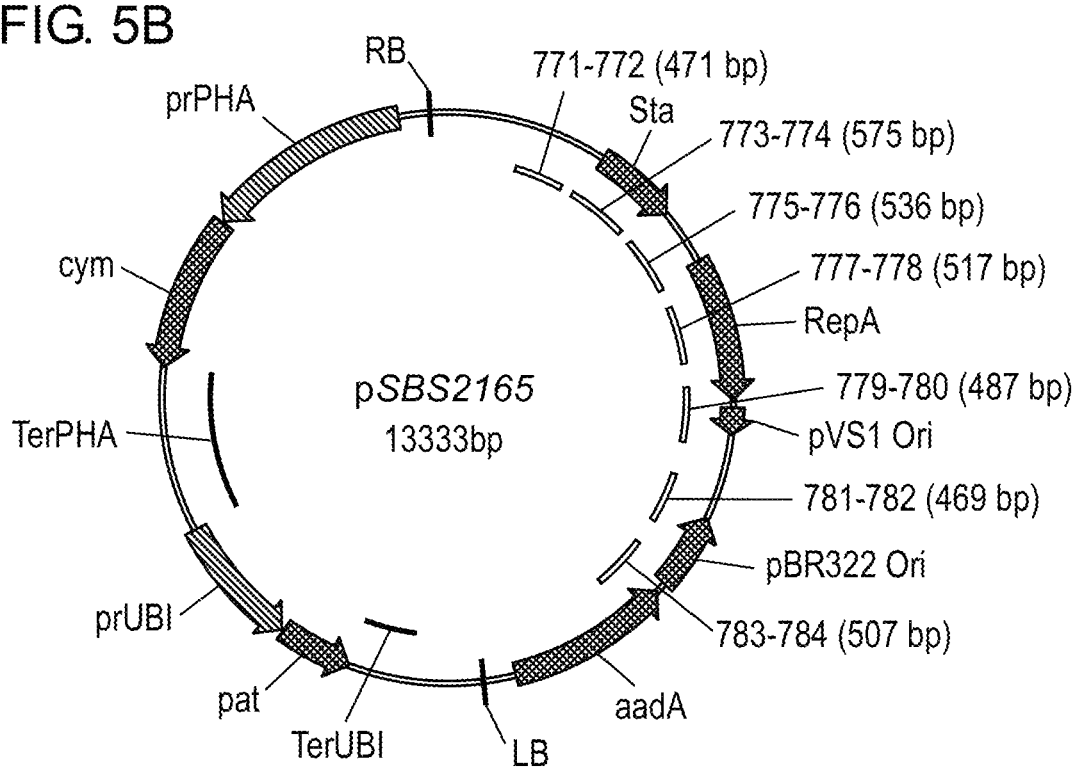

For the latter procedure, two series of initiating oligonucleotides were designed to amplify overlapping regions of approximately 1200 bp (FIG. 5A) and 500 bp (FIG. 5B) located outside the T-DNA region.

Figure 6:
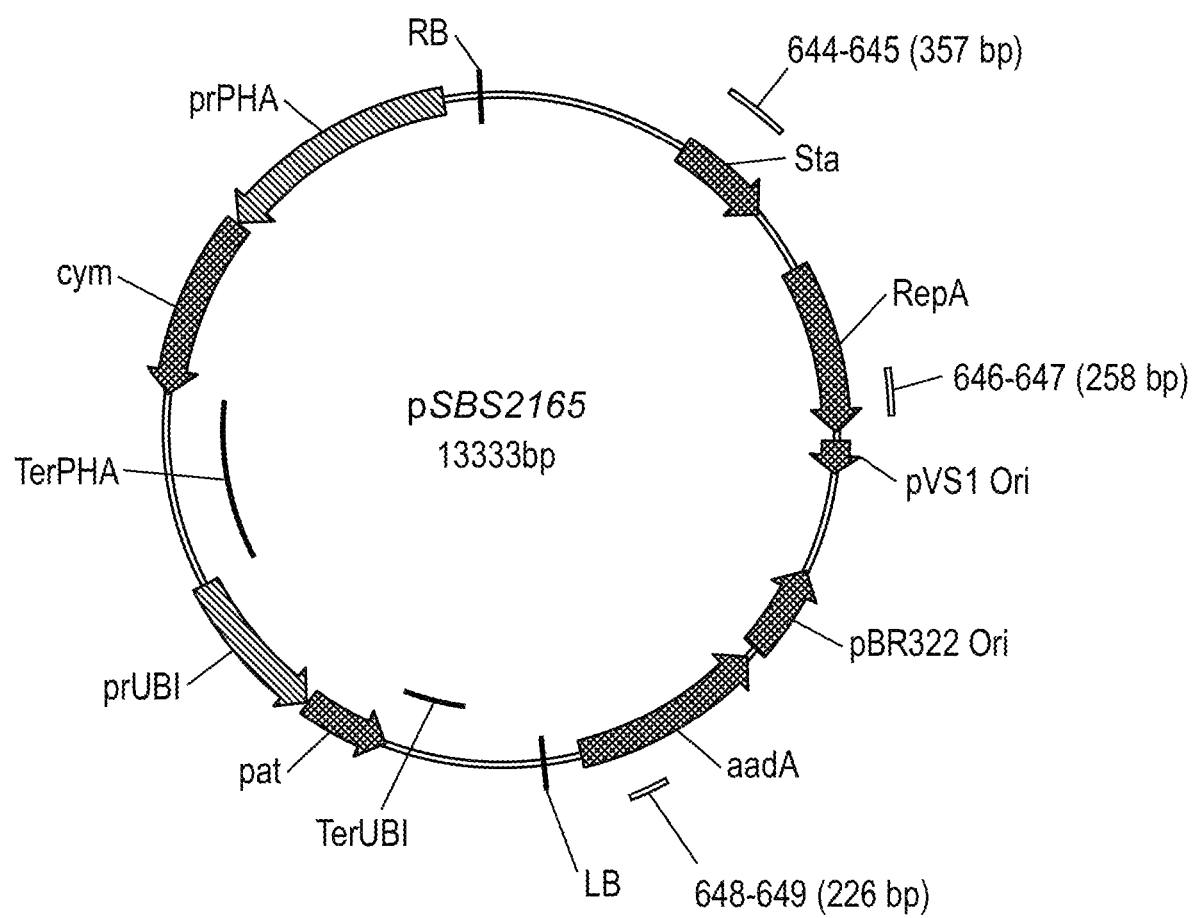
FIG. 6: Diagram of the amplified segment for the analysis of the presence of main non-T-DNA vector regions in events IND-1ØØØ3-4, IND-1ØØ15-7 and IND-1ØØØ3-4 x IND-1ØØ15-7. The non-solid lines indicate the amplicons of the main elements tested: sta, rep and aadA.

According to the results obtained, it can be expected that in the events IND-1ØØØ3-4 and IND-1ØØ15-7 there are no sequences of the plasmid pSBS2165 outside the T-DNA region, and the same would occur in the product of its crossing IND-1ØØØ3-4 x IND-1ØØ15-7. The latter was also confirmed by the amplification of key regions of the plasmid used (FIG. 6) where no amplification products were observed.

Identification of Insertion Sites and Flanking Sequences

In order to identify the insertion site in the T-DNA genome, known sequences of the T-DNA were used to design oligonucleotides that amplify in the direction of the unknown flanking sequences. The Tail-PCR (Thermal Asymmetric Interlaced) technique was used to characterize both insertion sites of event IND-1ØØ15-7 and the closest flank to the left border (LB) of T-DNA of event IND-1ØØØ3-4. However, using this technique, it was not possible to amplify and isolate the other flank of IND-1ØØØ3-4, that is, the closest to the right border (RB) of T-DNA.

FIGS. 7A, B and D show the sequences of the three flanks identified by Tail-PCR. In the flanks corresponding to IND-1ØØ15-7 the insert was determined to be in a gene that would code for an enzyme with glycoside hydrolase function. On the other hand, the flank identified of IND-1ØØØ3-4 suggested that the insert occurred in a gene region that would code for a hypothetical protein with chaperone function. Due to the lack of a fully assembled Carthamus tinctorious genome, in both cases the highest homology was found with probable coding regions of the Cynara cardunculus var. scolymus genome.

Due to the impossibility of determining the sequence of the remaining flank of the event IND-1ØØØ3-4 by Tail-PCR, attempts were made thru the specific amplification of the corresponding gene region with specific oligonucleotides. To do this, it used the sequence of the previously identified flank and the safflower transcriptome. This way, it was possible to identify the messenger RNA, transcribed by the gene interrupted by the T-DNA.

In the first instance, with oligonucleotides that hybridize at opposite ends of the transcript, the region corresponding to the untransformed Centennial genome was amplified by identifying the presence of an intron in the region of insertion. Next, with the gene sequence of interest now complete, progress was made in identifying the remaining flank of IND-1ØØØ3-4. This was done by PCR amplifications using oligonucleotides that targeted the corresponding T-DNA region (RB) and others in the opposite direction that hybridize over this T-DNA region.

However, PCR reactions using oligonucleotides that hybridized in the region adjacent to the RB of the T-DNA, corresponding to the phaseolin promoter sequences and the chymosin-coding region, were not successful. The latter raised the suspicion of a rearrangement in this region. Therefore, amplification was attempted with the use of oligonucleotides that hybridized in other regions of the T-DNA, in the expected or reverse direction. By means of this strategy, it was possible to identify a rearrangement in the T-DNA adjacent to the RB that comprises a fragment of the inverted phaseolin promoter and, adjacent to the intron previously detected in the safflower genome. These results made it possible to elucidate the sequence of the missing flank in the event IND-1ØØØ3-4 (FIG. 7C).

Segregation Analysis

As it is an event coming from a stack of events with independent inserts, the segregation analyses of both events were carried out by means of specific detection systems on the products of the crossing of homozygous individuals of IND-1ØØØ3-4 and IND-1ØØ15-7. In both cases, the DNA sequence inserted in the transformation events segregates the Mendelian way. This point details the studies carried out on F2 of the progeny obtained from the selfing of F1 from the mentioned crossing.

Figure 8A:
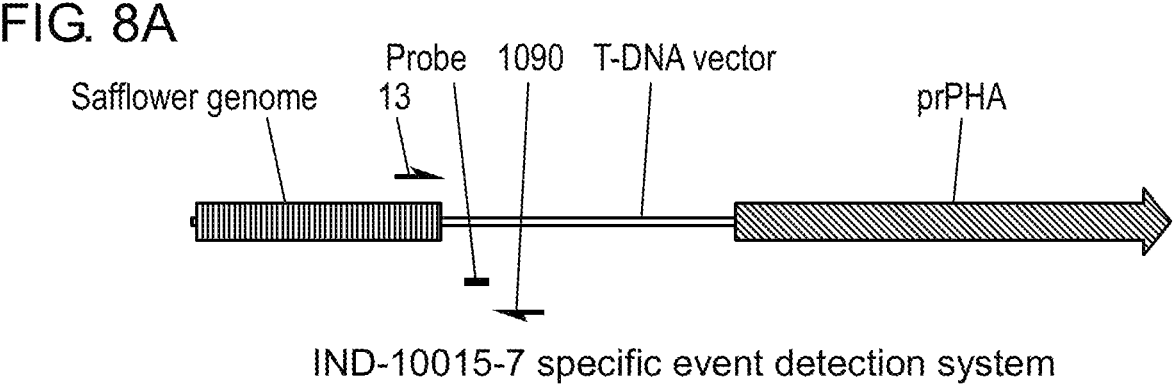
FIGS. 8A to 8D: Diagrams of event-specific detection system of event IND-1ØØ15-7 x IND-1ØØØ3-4 and corresponding non-GM alleles (WT). A) Event-specific detection system of IND-1ØØ15-7. Diagram of the genome-flanking region neighboring the RB of T-DNA and part of the prPHA. The position of the oligonucleotides and the probe used to detect the event is indicated in real time and specifically by PCR. B) Diagram of the locus at Centennial (WT). The position of the oligonucleotides used to detect the wild allele corresponding to IND-1ØØ15-7 is indicated in real time by PCR. C) Event-specific detection system of IND-1ØØØ3-4. Diagram of the genome-flanking region neighboring the RB of the T-DNA and part of the TerUBI. The position of the oligonucleotides and the probe used to detect the event is indicated in real time and specifically by PCR. D) Diagram of the locus at Centennial (WT). The position of the oligonucleotides used to detect the wild allele corresponding to IND-1ØØØ3-4 is indicated in real time by PCR. The non-solid lines indicate the position and size of the amplicons obtained by PCR.
Figure 8B:
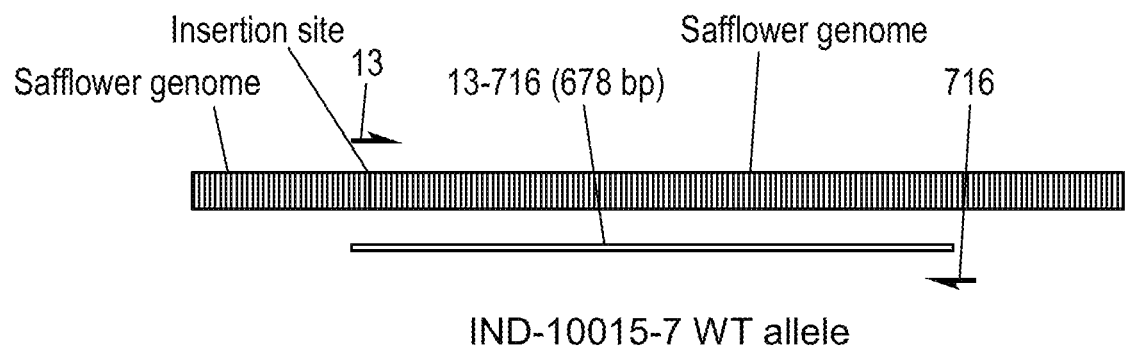
Figure 8C:
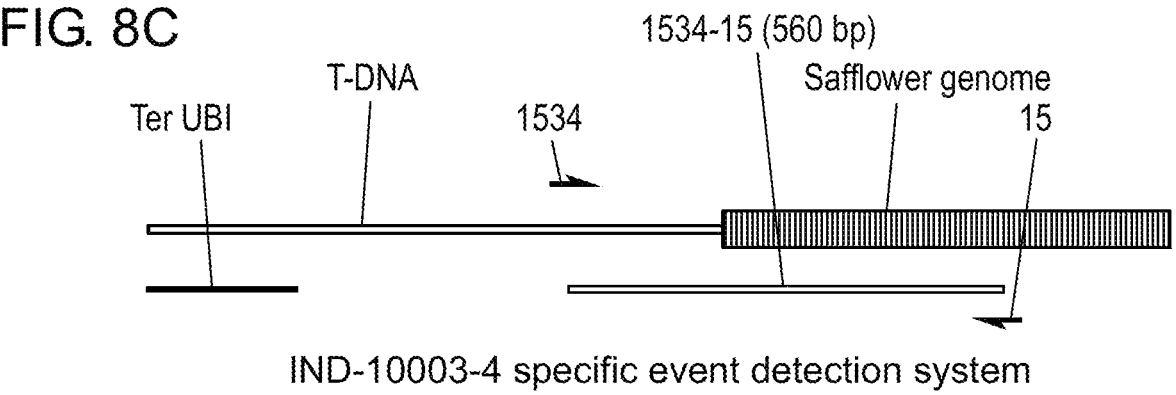
Figure 8D:
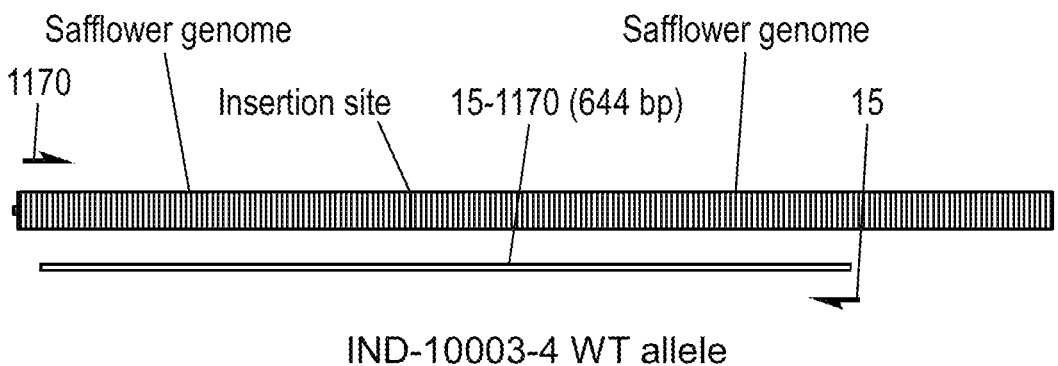

FIG. 8 shows the different fragments amplified by PCR, and the oligonucleotides used to detect the presence of the specific inserts of events IND-1ØØ15-7 and IND-1ØØØ3-4, FIGS. 8A and C of the specific event systems respectively. In addition to this, the diagrams corresponding to the regions of the unmodified safflower genome where the above-mentioned inserts were produced, FIGS. 8 B and D respectively, and the oligonucleotides used to detect these regions can be seen.

As a whole, these detection systems make it possible not only to detect the presence or absence of insertion events, but also the presence of unmodified regions and, therefore, to determine the zygosity of the individuals analyzed.

All these elements were used in the segregation studies carried out and in obtaining the molecular stacking of safflower events IND-1ØØØ3-4 x IND-1ØØ15-7.

In addition to detecting specific sequences of each insertion event, the coding regions of interest common to both cym and pat were detected, thus confirming that these segregate linked to each other and to the other elements detected in this analysis, i.e. the joint points (insertion sites) and their flanking regions.

The results obtained are detailed in Table 1. The plants were classified as Homozygous, Hemizygous or non-GM according to the results obtained from the detection of the specific joint points of IND-1ØØØ3-4 and IND-1ØØ15-7 and their corresponding wild type alleles.

A Chi-square test ($\chi 2$) of each insert was performed to evaluate the expected 1:2:1 genotypic segregation (Homozygous:Hemizygous:non-GM) in an F2 population for each of the events, IND-1ØØØ3-4 and IND-1ØØ15-7.

The Chi-square test is based on the comparison of observed frequencies with expected frequencies according to Mendelian principles of inheritance. The $\chi 2$ statistics was calculated as:

$$\chi 2 = \Sigma[(O-E)2/E]$$

where O=frequency observed of genotype and E=frequency expected of genotype. An $\alpha=0.05$ and 2 degrees of freedom were used. The results of this analysis for each intervening event are detailed in Table 1.

TABLE 1

Results obtained in the $\chi 2$ test for the events IND-1ØØ15-7 and IND-1ØØØ3-4 in the 241 F2 plants analyzed. TR: transgenic locus. Non-GM: non-genetically modified locus

| Event | Genotype | Expected Result (No of plants) | Expected Result (No of plants) | $\chi 2$ 0.95 | Statistic Value |
|---|---|---|---|---|---|
| IND-1ØØ15-7 | Homozygous (+/+) TR/TR | 60 | 48 | 5.99 | 0.159 |
| | Hemizygous (+/−) TR/Non-GM | 120 | 125 | | |

TABLE 1-continued

Results obtained in the χ2 test for the events
IND-1ØØ15-7 and IND-1ØØØ3-4
in the 241 F2 plants analyzed. TR: transgenic locus.
Non-GM: non-genetically modified locus

| Event | Genotype | Expected Result (No of plants) | Expected Result (No of plants) | χ2 0.95 | Statistic Value |
|---|---|---|---|---|---|
| | Homozygous (−/−) Non-GM/Non-GM | 60 | 68 | | |
| IND-1ØØØ3-4 | Homozygous (+/+) TR/TR | 60 | 57 | 5.99 | 0.829 |
| | Hemizygous (+/−) TR/Non-GM | 120 | 125 | | |
| | Homozygous (−/−) Non-GM/Non-GM | 60 | 59 | | |

The values of $\chi 2$ were less than 5.99 (gl=2, $\alpha$=0.05) thus indicating no statistically significant difference between the observed and expected results under the Mendelian segregation 1:2:1 for the analyzed data.

Post-Crossing Integrity and Stability

To verify that the insertion and T-DNA remain unaltered over generations, after the stacking of both events their complete sequence, between one insert site and another, was characterized in segregating F2 individuals for each of the insert events, IND-1ØØØ3-4 or IND-1ØØ15-7. Therefore, these plants result from the selfing of F1 from crossing between homozygous individuals of events IND-1ØØØ3-4 and IND-1ØØ15-7. Thus, while in F1 both inserts are present in all plants, constituting the molecular stack of safflower events IND-1ØØØ3-4 x IND-1ØØ15-7, after segregation in F2 the presence of only one of the inserts is detected in some plants, and these are the ones used in the present study.

In general, technically this was done by overlapping amplicons and sequencing them with Sanger on six F2 plants, which, as previously mentioned, had the insert of only one of the events, IND-1ØØØ3-4 or IND-1ØØ15-7. In these plants, the nucleotide sequences of both the inserts and their flanks were verified.

Analysis of Integrity and Identity Between the Sequences Present in the Molecular Stack of Safflower Events IND-1ØØØ3-4 x IND-1ØØ15-7 and the T-DNA of Plasmid After the sequences of insertion events present in the molecular stack of safflower events IND-1ØØØ3-4 x IND-1ØØ15-7 were verified, these were compared with the T-DNA sequence corresponding to the plasmid pSBS2165 used in the transformation and obtaining process of the transgenic safflower plants expressing CYM and PAT.

Figure 9:
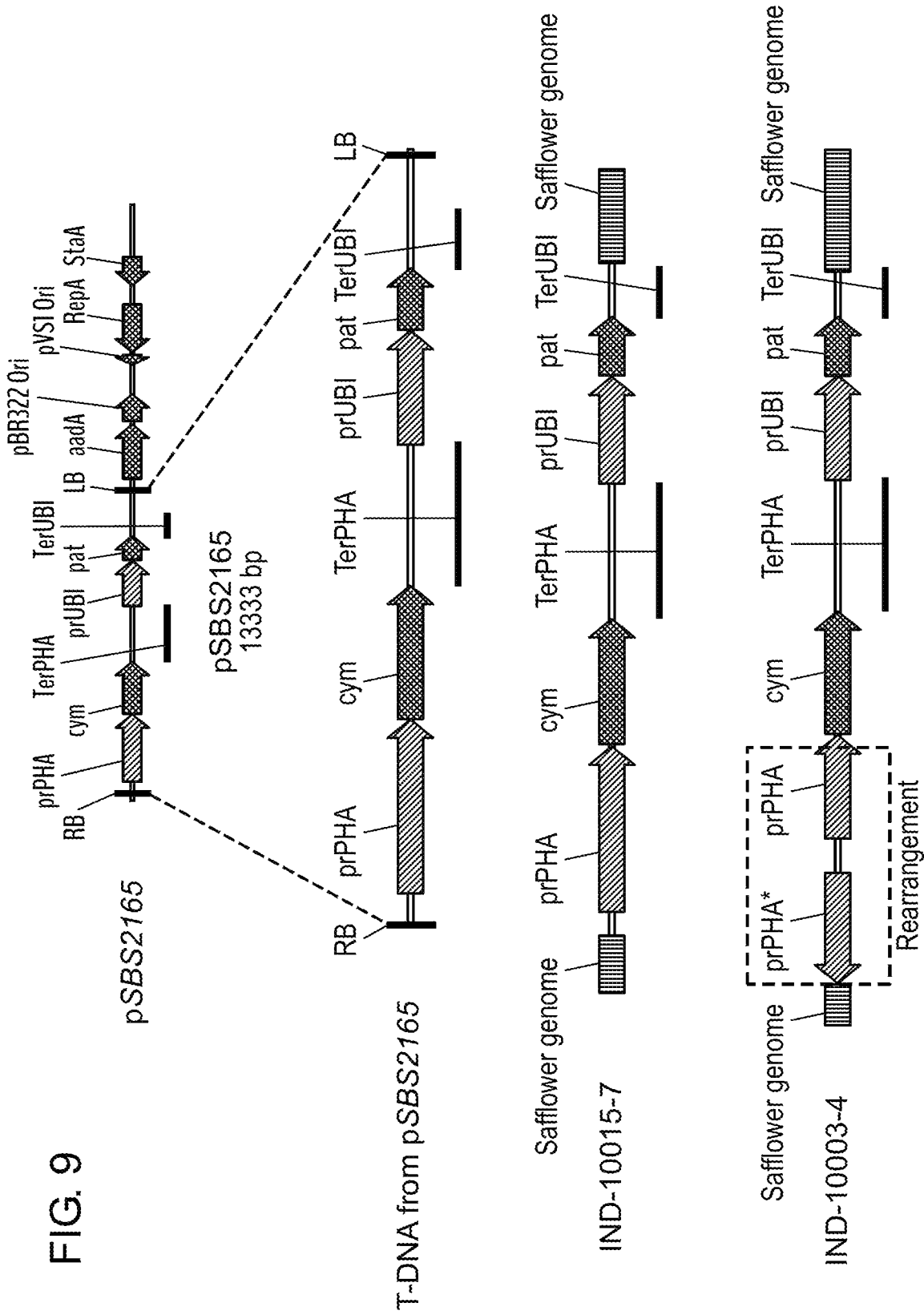
FIG. 9: Comparison between the maps of the T-DNA region and the inserts of the events IND-1ØØ15-7 and IND-1ØØØ3-4. Expression-promoting regions at the transcriptional level in lightly shaded boxes, protein-coding regions in more heavily shaded boxes and flanking regions in boxes with vertical line shading. The solid lines indicate the terminators at the transcriptional level. In the event IND-1ØØØ3-4, the region involving a re-arrangement is indicated in a fuchsia box: prPHA*, inverted and incomplete phaseolin promoter. prPHA, incomplete phaseolin promoter in the right direction.

FIG. 9 shows that while in the insert in IND-1ØØ15-7 the T-DNA sequence of the plasmid remained practically unchanged, in the insert corresponding to IND-1ØØØ3-4 changes involving the phaseolin-promoting region are detected.

The phaseolin promoter (prPHA) in the plasmid used in the transformation directing the expression of the CYM coding region is made up of 1547 bp. The re-arrangement detected in IND-1ØØØ3-4 led to the insert of 1064 bp upstream the transcription start site and, reversely, it was called prPHA*. In addition, the sequence of the prPHA promoter directing the expression of cym was detected to be a shorter version of active 1005 bp and is properly located regarding the above-mentioned coding region.

Stability of Stacked Events in Successive Generations of Selfing

Once the information is obtained indicating that in F2 individuals from the crossing between IND-1ØØØ3-4 and IND-1ØØ15-7 the inserts were intact and stable with respect to the parents, their stability was analyzed over successive generations of selfing of plants from the molecular stack of safflower events IND-1ØØØ3-4 x IND-1ØØ15-7.

To this end, individuals belonging to homozygous lines of generations F4, F6 and F8 were selected and the presence of the main elements of interest was detected. These regions included the coding regions of cym and pat, and useful sequences for event-specific detection that include flanking regions, both right and left for both events.

Figure 10A:
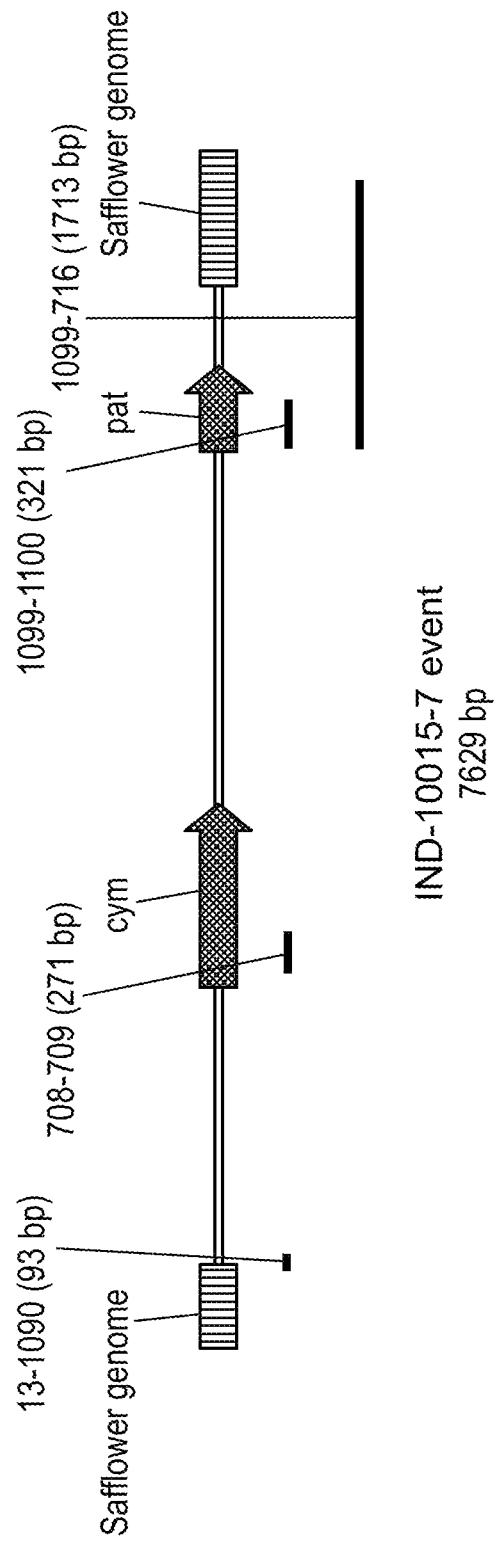
FIGS. 10A and 10B: Diagram of the elements detected in the stability analysis on the events IND-1ØØ15-7 and IND-1ØØØ3-4. Detected coding regions belonging to the T-DNA, cym and pat, heavily shaded, and flanking sequences corresponding to the safflower genome in the two insertion events with vertical line shading. The horizontal solid lines indicate the amplicons obtained by PCR, and in brackets the size in base pairs (bp) and oligonucleotides used.
Figure 10B:
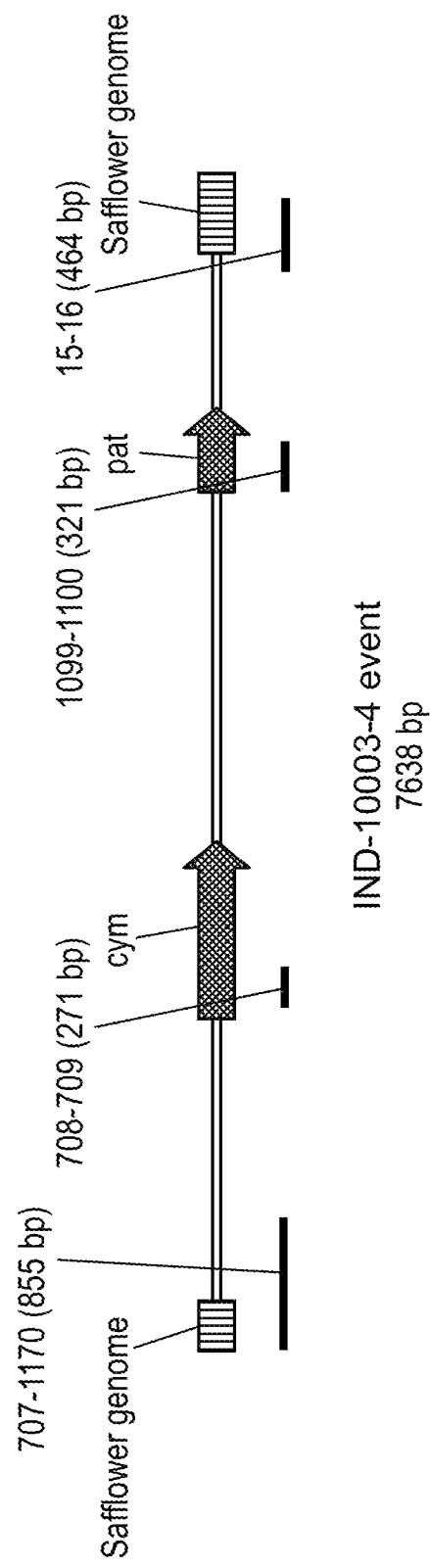

Both oligonucleotides and amplified regions are outlined in FIG. 10. They are partly the same ones used in the F2 segregation analysis, which were also used to identify homozygous individuals for both events that gave rise to F3 homozygous lines that originated the generations used in this study.

All the plants used in this analysis, 20 per generation, were homozygous for both insertion events and, therefore, all the elements analyzed were detected in them: the pat and cym coding regions and the four event-specific sequences.

Example 4: Useful Methods for Identifying IND-1ØØØ3-4 x IND-1ØØ15-7 in One Sample Molecular biology techniques involving amplification of specific DNA fragments by polymerase chain reaction (PCR) are used to identify the presence/absence of the event and the insert sites (joint points) (JP). The methodologies used, as well as the reaction mixes and amplification programs required for each determination, are detailed below.

Detection of the Insert Sites (Joint Points) (JP)

Figure 11:
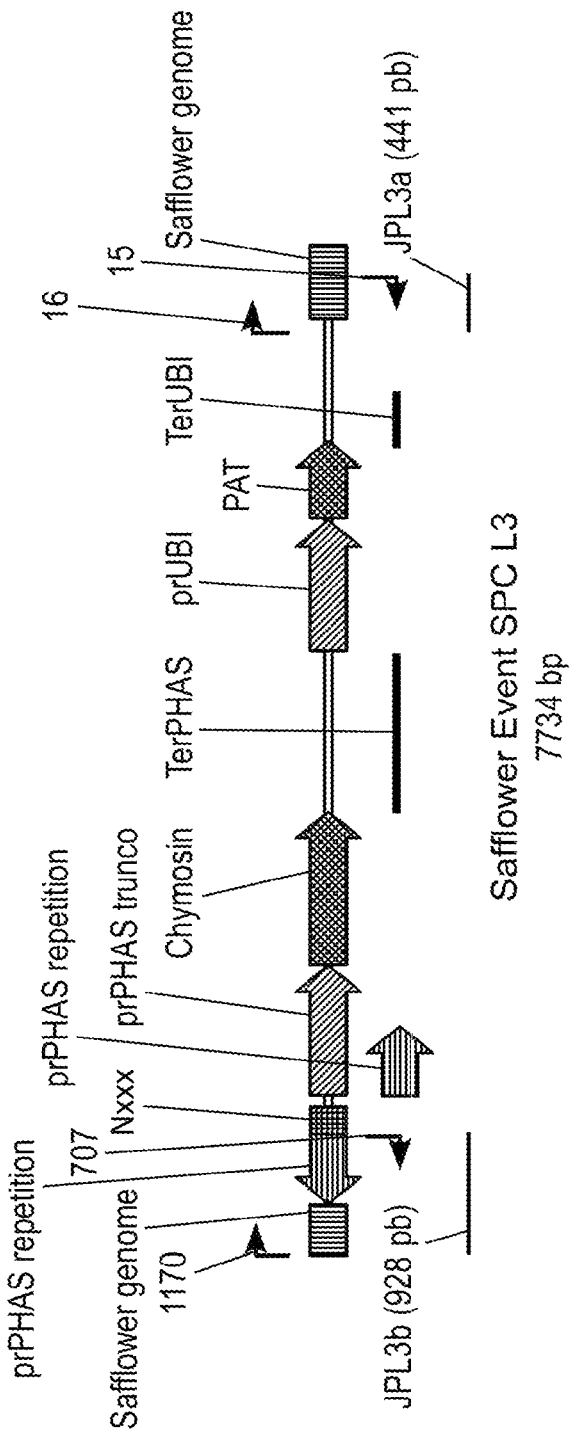
FIG. 11: Detection of the joint points (JP) of the event IND-1ØØØ3-4, left border of the T-DNA (JPL3a) and right border of the T-DNA (JPL3b). Both JPL3a and JPL3b are evaluated by end time PCR. The diagram shows the specific oligonucleotides and the sizes of the amplicons.
Figure 12:
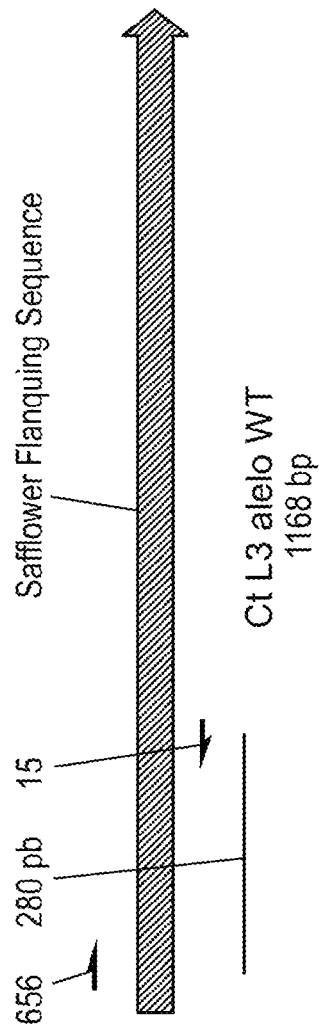
FIG. 12: Detection of the WT allele corresponding to the event IND-1ØØØ3-4. This region is evaluated by end time PCR. The specific oligonucleotides and the size of the amplicon are indicated in the diagram.

The presence of the insert site of event IND-1ØØØ3-4 is determined by the technique of end time PCR, using the primers of SEQ ID NO: 6 and 7 for the left border insert site of the T-DNA of event IND-1ØØØ3-4 (JPL3a) and the primers of SEQ ID NO: 8 and 9 for the right border insert site of the T-DNA of event IND-1ØØØ3-4 (JPL3b) (FIG. 11). The WT allele of IND-1ØØØ3-4 is also detected by end-time PCR, using the primers of SEQ ID NO: 6 and 10 (FIG. 12).

Figure 13:
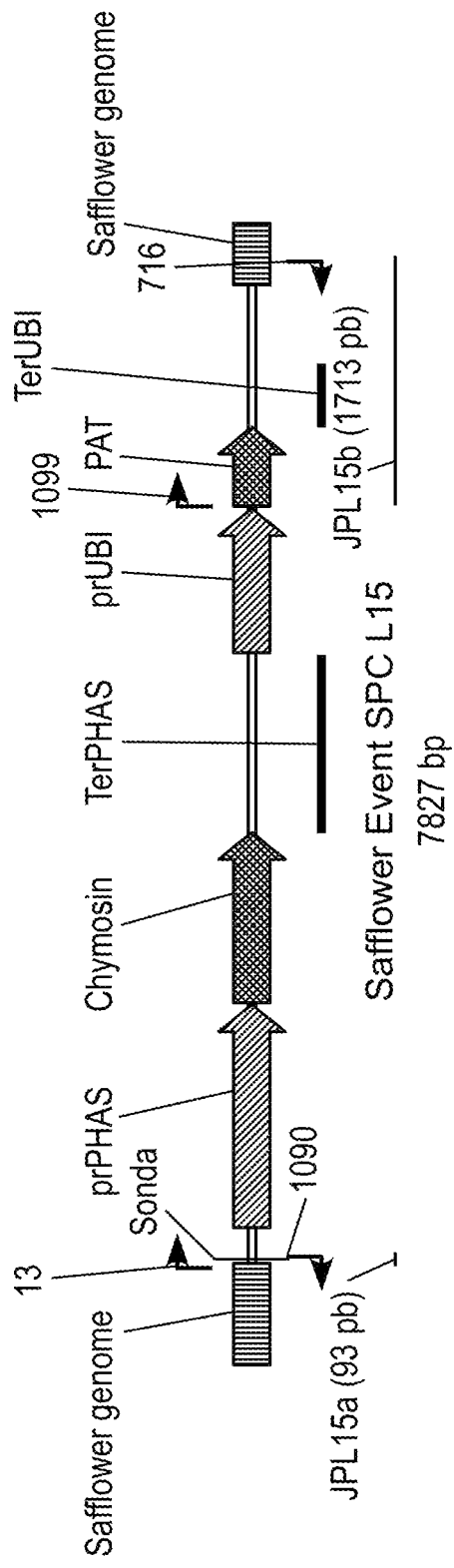
FIG. 13: Detection of the joint points (JP) of event IND-1ØØ15-7, left border of T-DNA (JPL15a) and right border of T-DNA (JPL15b). JPL15a is evaluated by qPCR and JPL15b is evaluated by end time PCR. The diagram shows the specific oligonucleotides, probe and amplicon sizes.
Figure 14:
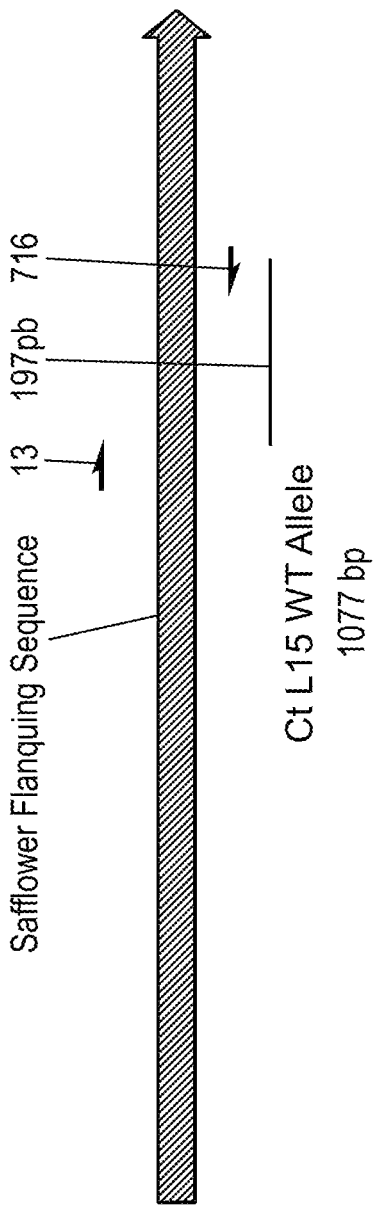
FIG. 14: Detection of the WT allele corresponding to the event IND-1ØØ15-7. This region is evaluated by end time PCR. The specific oligonucleotides and the size of the amplicon are indicated in the diagram.

As for event IND-1ØØ15-7, the detection of the insertion site of the left border of the T-DNA of the event (JPL15a) is performed by the real-time PCR technique (qPCR), using the primers of SEQ ID NO: 11 and 12 and the Taqman probe of SEQ ID NO: 13, as shown in FIG. 13. The detection of the insertion site of the right border of the T-DNA of event IND-1ØØ15-7 (JPL15b) is performed by the end-time PCR technique, using the primers of SEQ ID NO: 14 and 15 (FIG. 13). The WT allele of event IND-1ØØ15-7 is also detected by end-time PCR, using the primers of SEQ ID NO: 11 and 14 as shown in FIG. 14.

For end-time PCR, the reaction mix is used as shown in Table 2, and the amplification program in Table 3.

TABLE 2

Reaction mix End time PCR

| VOLUME | REAGENT |
|---|---|
| 2 µL | Genomic DNA (100 ng) |
| 2 µL | PCR Buffer (10X) |
| 1.6 µL | MgCl2 (25 mM) |

TABLE 2-continued

Reaction mix End time PCR

| VOLUME | REAGENT |
|---|---|
| 1 μL | Primer F (10 μM) |
| 1 μL | Primer R (10 μM) |
| 0.4 μL | dNTPs(10 mM) |
| 0.1 μL | Taq polymerase (5 U/μl) |
| 11.9 μL | mqH2O |
| 20 μL | Total reaction volume |

TABLE 3

Amplification Program

| Stage | Temperature (° C.) | Time | No cycles |
|---|---|---|---|
| Initial Denaturing | 94° C. | 240" | 1 |
| Denaturing | 94° C. | 30" | 30 cycles |
| Anneal | 55° C. | 30" | |
| Extention | 72° C. | 30" | |
| End Reaction | 4° C. | 120" | 1 |

PCR reactions are displayed by horizontal electrophoresis on 1.5% agarose gel and sodium borate buffer. The electrophoretic run is performed at 120 V for 30 minutes.

For real-time PCR (qPCR), the reaction mix in Table 4 and the amplification program in Table 5 are used.

TABLE 4 qPCR Reaction Mix

| VOLUME | REAGENT |
|---|---|
| 2 μL | Genomic DNA (100 ng/μl) |
| 5.9 μL | (H₂O)dd |
| 10 μL | qPCRSuperMix (2 X) |
| 0.5 μL | bar Probe (10 μM) |
| 0.8 μL | bar Primer F (10 μM) |
| 0.8 μL | bar Primer R (10 μM) |
| 20 μL | Total reaction volume |

TABLE 5

Amplification Program

| Temp (° C.) | Time | Temp. Ramp (° C./s) |
|---|---|---|
| 95 | 5 minutes | 4.4 |
| 95 | 15 seconds | 4.4 |
| 55 | 30 seconds | 1.8 |
| 72 | 1 second | 4.4 |
| 10 | 5 minutes | 2.2 |

By detecting one of the insertion sites for each event and the WT allele for both events, it is possible to determine the genotype of the individual; IND-1ØØØ3-4, IND-1ØØ15-7 or IND-1ØØØ3-4 x IND-1ØØ15-7.

Event Detection

In order to determine event IND-1ØØØ3-4 the primers used are those of SEQ ID NO: 16 and 17, an amplicon of 108 bp is obtained, using the probe of SEQ ID NO: 18.

For event IND-1ØØ15-7 the primers used are those of SEQ ID NO: 11 and 12, and the probe of SEQ ID NO: 13, and an amplicon of 93 bp is obtained.

For these determinations, real-time PCR (qPCR), the reaction mix in Table 6 and the amplification program in Table 7 are used.

TABLE 6 qPCR Reaction Mix

| Reagent | Final Concentration | μL/ reaction |
|---|---|---|
| LightCycler ® 480 Probes Master (Roche) (2X) | 1X | 5 μL |
| Direct Primer (10 μM) | 0.4 μM | 0.4 μL |
| Reverse Primer (10 μM) | 0.4 μM | 0.4 μL |
| Probe (10 μM) | 0.25 μM | 0.25 μL |
| H₂0 nuclease-free | — | 2.95 μL |
| DNA (100 ng) | — | 1 μL |
| End reaction volume | | 10 μL |

TABLE 7

Amplification Program

| Temp (° C.) | Time | Temp. Ramp (° C./s) | Number of cycles |
|---|---|---|---|
| 95 | 5 minutes | 4.4 | Denaturing |
| 95 | 15 seconds | 4.4 | 35 cycles qPCR |
| 55 | 30 seconds | 1.8 | |
| 72 | 10 seconds | 4.4 | |
| 10 | 5 minutes | 2.2 | Cooling |

Example 5: Agronomic Traits and Performance

To evaluate the agronomic traits and grain yield of molecular stacking of safflower events IND-1ØØØ3-4 x IND-1ØØ15-7 trials were conducted in 3 different locations in the period of 2014/2015 as shown in Table 8. The events were planted together with a Centennial, the control of the wild type and a number of conventional varieties. The materials sown included the molecular stacking of safflower events IND-1ØØØ3-4 X IND-1ØØ15-7, the untransformed control variety (Centennial) and commercial cultivars used as reference (Table 9). The trials were conducted following the usual practices of cultural management of the crop.

TABLE 8

Locations

| Site | City | Province | Type of occurrence | Planting date | Harvest date |
|---|---|---|---|---|---|
| VS | Villa Saboya | Buenos Aires | Hapludol Entico | 26 Aug. 2014 | 29 Jan. 2015 |
| BB | Bahia Blanca | Buenos Aires | Typical Haplustol | 30 Jul. 2014 | 28 Jan. 2015 |
| MC | Montecristo | Córdoba | Typical Haplustol | 7 Jul. 2014 | 21 Jan. 2015 |

TABLE 9

Entries evaluated in field trials

| Entries | Material Type |
|---|---|
| Safflower SPC_DC# | GM |
| Centennial | Control |
| S-518 | Commercial |

TABLE 9-continued

Entries evaluated in field trials

| Entries | Material Type |
|---|---|
| S-555 | Commercial |
| 9-ECR | Experimental |
| CW88 | Commercial |
| CW99 | Commercial |

Safflower SPC_DC: IND-1ØØØ3-4 × IND-1ØØ15-7

Trial Design

The plots were sown using a randomized complete block design with four replicates. Each plot consisted of four rows spaced 0.4 meters apart (Villa Saboya) or 0.52 meters apart (Monte Cristo and Bahia Blanca) and 10 meters long. The seeds were treated with Maxim Evolution (100 cc/100 kg seed) before planting. The planting density was 40 plants m-2, approximately. The trials plots were surrounded by a four-furrow border of a commercial material (S-719). An electric fence was installed in each trial plot to prevent animals from entering the plots.

Seed increments of the transgenic event were performed in Roldan on two planting dates and in Villa Saboya. In each location, 180 m2 were planted.

The weather conditions during the growing season at each site are shown in Table 10. At each site, appropriate agrochemicals were applied both before planting and during the crop cycle to control weeds, pests and diseases (Table 11).

TABLE 10

Rainfall recorded at each site during the 2014 season

| | Rainfall (mm) | | | | | | |
|---|---|---|---|---|---|---|---|
| | 2014 | | | | | 2015 | |
| Site | August | September | October | November | December | January | Total |
| VS | 0 | 48 | 71 | 51 | 97 | 195 | 462 |
| BB | 95 | 58 | 165 | 101 | 48 | 86 | 553 |
| MC | — | 9 | 51 | 39 | 52 | 125 | 276 |

TABLE 11

Agrochemicals used to control weeds, pests and diseases during the 2014 season at each site

| Date | Site | Rate of application | Product (Commercial name) | Purpose |
|---|---|---|---|---|
| 26 Aug. 2014 | VS | 3 L ha−1 | GlyPhosate (Roundup Full II) | Pre-Planting herbicide |
| 21 Nov. 2014 | VS | 0.5 L ha−1 | Azoxystrobin + Ciproconazole (Amistar xtra) | Fungicide |
| 21 Nov. 2014 | VS | 0.5 L ha−1 | Clorpirifós (Nurfam) | Insecticide |
| 21 Nov. 2014 | VS | 0.125 L ha−1 | Alfacipermetrina (Fastac 10) | Insecticide |
| 7 Jul. 2014 | MC | 100 Kg ha−1 | Fosfato Monoamónico | Fertilizer |
| 14 Nov. 2014 | MC | 0.5 L ha−1 | Azoxystrobin + Tebuconazole (Custodia) | Fungicide |
| 14 Nov. 2014 | MC | 0.25 L ha−1 | Imidacloprid (Matrero 35) | Insecticide |
| 12 Dec. 2014 | MC | 0.5 L ha−1 | Azoxystrobin + Tebuconazole (Custodia) | Fungicide |
| 23 Jul. 2014 | BB | 2.5 Kg ha−1 | Gliphosate (Round Up Ultramax) | Pre-Planting herbicide |
| 20 Nov. 2014 | BB | 0.5 L ha−1 | Azoxystrobin + Ciproconazole (Amistar xtra) | Fungicide |
| 20 Nov. 2014 | BB | 0.5 L ha−1 | Clorpirifós (Nurfam) | Insecticide |
| 20 Nov. 2014 | BB | 0.125 L ha−1 | Alfacipermetrina (Fastac 10) | Insecticide |
| 16 Jan. 2015 | BB | 1.5 Kg ha−1 | Gliphosate (Round Up Ultramax) | Drying |
| 16 Jan. 2015 | BB | 0.5 L ha−1 | Clorpirifós (Nurfam) | Insecticide |
| 16 Jan. 2015 | BB | 0.2 L ha−1 | Imidacloprid (Confidor 350SC) | Insecticide |

VS: Villa Saboya;
MC: Monte Cristo,
BB: Bahía Blanca

Data Collection

The data collected in the trials include days to emergence, seedling vigor, initial and final stand of plants, phenology, plant height at two points in the cycle, lodging, grain moisture at harvest and yield (Table 12).

Samples were collected from different tissues at different times for analyses of protein expression and feed and grain composition (Table 12). The tissues used to measure the expression of the expressed proteins were preserved at −20° C., except for the grain, which was kept at room temperature for, further compositional analysis. The plants collected for fodder composition determinations were dried in an oven for 2 or 3 days at 50-60° C. and preserved in a fresh and dry place, for its later transfer to the laboratory specialized in compositional analysis.

TABLE 12

List of agronomic parameters measured

| Trait | Scale |
|---|---|
| Days to emergence (days) | Date recorded when 50% of plants in each plot were emerging. Days since planting calculated |
| Early and final plant stand (plants · m−1) | Emerged plants in 1 meter is calculated by the total number of plants of the two central rows divided by the row's length |
| Seedling vigour (1-9 scale) | 1-3: 3 cm of diameter rosette, small leaves, low development and pale green colour, very low or low vigour. 4-6: 10 cm of diameter rosette, average leaf size, deep green colour, medium vigour. 7-9: more than 10 cm of diameter rosette, large leaves, very deep green colour, and high vigour. |
| Days to stem elongation (days) | Date recorded when 50% of plants in each plot were stem elongation. Days since planting calculated |
| Days to floral bud (days) | Date recorded when 50% of plants in each plot were floral bud. Days since planting calculated |
| Plant height (cm) on floral bud | Recorded the average height of five representative plants of each plot on floral bud |
| Days to flowering (days) | Date recorded when 50% of plants in each plot were flowering. Days since planting calculated |
| Days to maturity (days) | Date recorded when 50% of plants in each plot reach maturity. Days since planting calculated |
| Lodging Score (1-9) | 1 more than 90% of plant lying flat; 2-3 more than 75% of plants lying flat; 4-5 more than 50% of plants lying flat; 6-7 more than 25% of plants lying flat; 8 less than 10% of plants lying flat 9 all plants erect |
| Plant height (cm) to maturity | Recorded the average height of five representative plants of each plot to maturity |
| Final plant stand (plants · m−1) | Emerged plants in 1 meter is calculated by the total number of plants of the two central rows divided by the row's length |
| Grain moisture (%) | Moisture (%) of a sample from bulk yield |
| Yield (Kg · ha−1) | Recorded the weight in grams of grain harvested from the two middle rows of each plot. Yield (Kg/ha) calculated |
| Disease damage (1-9 scale) | 1-9 Rating score; 0 None, no symptoms observed; 1-3 Mild, very little disease injury (<10%) visible; 4-6 Moderate, noticeable plant tissue damage (10%-30%); 7-9 Severe, significant plant tissue damage (>30%) |
| Insect damage (0-5) | 0-5 Rating score; 0 None, no symptoms observed; 1 (1-20%) slight, symptoms not damaging to plant development; 2 (21-40%) and 3 (41-60%) moderate (intermediate between slight and severe); 4 (61-80%) and 5 (>80%) severe (symptoms damaging to plant development) |
| Tissue sampling for protein expression | Estadio roseta: hoja Estadio cosecha: grano |
| Forage sampling for compositional analysis | Aerial biomass sampling Grain sampling at harvest |

Statistical Analysis

For each site, the transgenic event and control data were analyzed by ANOVA using the inputs and blocks as fixed factors and a significance level of 95% (p=0.05). The values from the commercial varieties were used to define the reference range. In addition, a combined analysis involving genotype interaction by environment was performed.

Disease and insect damage data were analyzed by environment/site given the natural variation that exists between sites regarding these variables.

Results

Statistical analysis revealed that there was no environmental genotype interaction for any of the traits evaluated, except for grain moisture (p=0.0044, Table 13). When the sites were analyzed separately (Tables 14, 15 and 16), both in Villa Saboya and in Bahia Blanca grain moisture was higher for the transgenic event. In Villa Saboya, the grain moisture values are within the range observed in commercial varieties, while in Bahia Blanca, the moisture value is 0.3 higher than the upper range observed for the varieties. Although this value is higher than the range for that location, the difference can be considered as biologically negligible. On the other hand, in the combined site analysis the grain moisture values for the event are within the reference ranges.

For the analysis of individual sites, in addition to the moisture differences discussed in the previous paragraph, significant differences were observed in plant height at maturity for Monte Cristo. The transgenic event showed a higher plant height (5.2 cm) with respect to the control. However, the height values observed at that location are within the range observed in the references.

With respect to ecological interactions, no significant differences in insect damage and disease were observed in any of the locations (Table 17, 18 and 19).

TABLE 13

| Phenotypic traits Combined site | | | |
|---|---|---|---|
| | Mean (stándar error) | | |
| Phenotypic Characteristic (units) | IND-1ØØØ3-4 × IND-1ØØ15-7 | Centennial | Reference range |
| Days to emergence (days) | 17.8 ± 2.3 | 19.9 ± 2.6 | 10.3-27.5 |
| Seedling vigour (1-9 scale) | 2.1 ± 0.3 | 2.0 ± 0.3 | 1.0-6.5 |
| Early plant stand (plants · 2 m−1) | 33.8 ± 2.8 | 29.7 ± 1.8 | 22.8-43.5 |
| Days to stem elongation (days) | 67.4 ± 3.6 | 66.5 ± 4.2 | 46.5-82.8 |
| Days to floral bud (days) | 115.9 ± 6.4 | 114.8 ± 6.3 | 82.5-133.5 |
| Plant height (cm) in floral bud | 62.4 ± 1.6 | 59.0 ± 2.8 | 45.0-75.4 |
| Days to flowering (days) | 123.1 ± 8.5 | 121.1 ± 7.8 | 98.0-146.8 |
| Days to maturity (days) | 150.0 ± 5.2 | 150.3 ± 4.9 | 124.5-170.5 |
| Lodging Score (1-9) | 9.0 ± 0.0 | 8.8 ± 0.1 | 7.0-9.0 |
| Plant height (cm) to maturity | 65.3 ± 1.1 | 66.8 ± 2.3 | 60.3-83.5 |
| Final plant stand (plants · m−1) | 26.3 ± 1.6 | 23.1 ± 1.4 | 17.0-44.0 |
| Grain moisture (%) | 9.5 ± 0.5 | 8.7 ± 0.3 * | 7.8-15.1 |
| Yield (Kg · ha−1) | 1222.3 ± 61.7 | 1321.8 ± 120.5 | 965.4-2045.1 |

* Significant differences (p < 0.05)

TABLE 14

| Phenotypic traits. Villa Saboya | | | |
|---|---|---|---|
| | Mean (stándar error) | | |
| Phenotypic Characteristic (units) | IND-1ØØØ3-4 × IND-1ØØ15-7 | Centennial | Reference range |
| Days to emergence (days) | 12.0 ± 0.4 | 13.0 ± 0.4 | 10.3-12.8 |
| Seedling vigour (1-9 scale) | 2.5 ± 0.3 | 2.3 ± 0.5 | 2.3-5.0 |
| Early plant stand (plants · 2 m−1) | 37.3 ± 2.7 | 35.8 ± 1.3 | 26.3-43.5 |
| Days to stem elongation (days) | 51.8 ± 0.5 | 48.3 ± 1.4 | 46.5-78.5 |
| Days to floral bud (days) | 86.0 ± 0.0 | 85.3 ± 0.8 | 82.5-85.3 |
| Plant height (cm) in floral bud | 64.0 ± 2.8 | 66.1 ± 1.2 | 63.2-75.4 |
| Days to flowering (days) | 100.8 ± 0.8 | 100.5 ± 1.4 | 98.0-102.3 |
| Days to maturity (days) | 127.8 ± 1.8 | 129.3 ± 0.6 | 124.5-127.8 |
| Lodging Score (1-9) | 9.0 ± 0.0 | 9.0 ± 0.0 | 9.0-9.0 |
| Plant height (cm) to maturity | 62.9 ± 0.9 | 69.0 ± 1.9 | 60.3-70.7 |
| Final plant stand (plants · m−1) | 22.5 ± 1.8 | 24.5 ± 2.3 | 27.0-30.0 |
| Grain moisture (%) | 8.6 ± 0.1 | 8.2 ± 0.1 * | 8.0-8.3 |
| Yield (Kg · ha−1) | 1295.0 ± 133.2 | 1613.4 ± 210.9 | 1499.4-2045.1 |

* Significant differences (p < 0.05)

TABLE 15

| Phenotypic traits. Montecristo | | | |
|---|---|---|---|
| | Mean (stándar error) | | |
| Phenotypic Characteristic (units) | IND-1ØØØ3-4 × IND-1ØØ15-7 | Centennial | Reference range |
| Days to emergence (days) | — ± — | — ± — | — |
| Seedling vigour (1-9 scale) | 2.8 ± 0.8 | 2.8 ± 0.8 | 3.5-6.5 |
| Early plant stand (plants · 2 m−1) | 32.6 ± 2.2 | 25.3 ± 2.7 | 36.8-42.3 |
| Days to stem elongation (days) | 71.8 ± 0.3 | 75.0 ± 1.8 | 68.0-70.0 |
| Days to floral bud (days) | 129.3 ± 1.2 | 129.5 ± 2.3 | 126.0-130.8 |
| Plant height (cm) in floral bud | 65.7 ± 1.8 | 61.0 ± 4.7 | 59.0-70.8 |
| Days to flowering (days) | — ± — | — ± — | — |
| Days to maturity (days) | 169.3 ± 0.5 | 168.5 ± 0.9 | 168.0-170.5 |
| Lodging Score (1-9) | 9.0 ± 0.0 | 8.5 ± 0.3 | 7.0-7.5 |
| Plant height (cm) to maturity | 67.7 ± 2.5 | 62.5 ± 2.7 * | 61.3-72.3 |
| Final plant stand (plants · m−1) | 30.8 ± 2.3 | 24.8 ± 2.8 | 35.3-40.5 |
| Grain moisture (%) | 8.3 ± 0.1 | 8.1 ± 0.1 | 7.8-8.4 |
| Yield (Kg · ha−1) | 1149.7 ± 73.3 | 1030.2 ± 21.1 | 965.4-1404.8 |

* Significant differences (p < 0.05)

TABLE 16

| Phenotypic traits. Bahía Blanca | | | |
|---|---|---|---|
| | Mean (stándar error) | | |
| Phenotypic Characteristic (units) | IND-1ØØØ3-4 × IND-1ØØ15-7 | Centennial | Reference range |
| Days to emergence (days) | 21.0 ± 1.4 | 26.0 ± 0.8 | 17.0-27.5 |
| Seedling vigour (1-9 scale) | 1.0 ± 0.0 | 1.0 ± 0.0 | 1.0-4.0 |
| Early plant stand (plants · 2 m−1) | 32.0 ± 8.4 | 28.0 ± 2.8 | 22.8-37.3 |
| Days to stem elongation (days) | 78.8 ± 3.3 | 76.3 ± 4.2 | 69.0-82.8 |
| Days to floral bud (days) | 132.5 ± 1.5 | 129.5 ± 1.5 | 128.0-133.5 |
| Plant height (cm) in floral bud | 57.5 ± 2.5 | 50.0 ± 4.1 | 45.0-67.5 |
| Days to flowering (days) | 145.5 ± 2.5 | 141.8 ± 1.3 | 134.0-146.8 |
| Days to maturity (days) | 153.0 ± 0.0 | 153.0 ± 0.0 | 148.0-153.0 |
| Lodging Score (1-9) | 9.0 ± 0.0 | 9.0 ± 0.0 | 9.0-9.0 |
| Plant height (cm) to maturity | 65.3 ± 1.6 | 68.0 ± 5.9 | 65.4-83.5 |
| Final plant stand (plants · m−1) | 20.0 ± 2.3 | 25.8 ± 3.0 | 17.0-44.0 |
| Grain moisture (%) | 11.6 ± 0.6 | 9.8 ± 0.3 * | 8.0-15.1 |
| Yield (Kg · ha−1) | — ± — | — ± — | — |

* Significant differences (p < 0.05)

TABLE 17

Disease and insect damage. Villa Saboya

| | | Mean (stándar error) | | |
|---|---|---|---|---|
| Damage agent | Phenological stages | IND-10003-4 × IND-10015-7 | Centennial | Reference range |
| Deseases | VRn | 0.0 ± 0.0 | 0.0 ± 0.0 | 0.0-0.0 |
| Insects | VRn | 0.0 ± 0.0 | 0.0 ± 0.0 | 0.0-0.0 |
| Deseases | BT | 3.0 ± 0.4 | 2.0 ± 0.6 | 2.0-2.8 |
| Insects | BT | 1.0 ± 0.0 | 1.0 ± 0.0 | 1.0-1.0 |
| Deseases | FL | 0.5 ± 0.5 | 0.0 ± 0.0 | 0.0-0.8 |
| Insects | FL | 0.0 ± 0.0 | 0.0 ± 0.0 | 0.0-0.0 |
| Insects | MF | 1.0 ± 0.0 | 1.0 ± 0.0 | 1.0-1.0 |

VRn: rosette;
BT: floral bud;
FL: flowering;
MF: physiological mature

TABLE 18

Disease and insect damage. Montecristo

| | | Mean (stándar error) | | |
|---|---|---|---|---|
| Damage agent | Phenological stages | IND-10003-4 × IND-10015-7 | Centennial | Reference range |
| Deseases | VRn | 0.0 ± 0.0 | 0.0 ± 0.0 | 0.0-0.0 |
| Insects | VRn | 0.0 ± 0.0 | 0.0 ± 0.0 | 0.0-0.0 |
| Deseases | BT | 1.5 ± 0.3 | 1.0 ± 0.0 | 1.0-1.5 |
| Insects | BT | 0.3 ± 0.3 | 0.5 ± 0.3 | 0.0-0.8 |
| Deseases | FL | 1.8 ± 0.3 | 2.0 ± 0.0 | 1.3-1.8 |
| Insects | FL | 0.0 ± 0.0 | 0.0 ± 0.0 | 0.0-0.0 |
| Insects | ET | 0.0 ± 0.0 | 0.0 ± 0.0 | 0.0-0.0 |

VRn: rosette;
BT: floral bud;
FL: flowering;
MF: physiological mature

TABLE 19

Disease and insect damage. Bahía Blanca

| | | Mean (stándar error) | | |
|---|---|---|---|---|
| Damage agent | Phenological stages | IND-10003-4 × IND-10015-7 | Centennial | Reference range |
| Deseases | VRn | 0.0 ± 0.0 | 0.0 ± 0.0 | 0.0-0.0 |
| Insects | VRn | 0.0 ± 0.0 | 0.0 ± 0.0 | 0.0-0.0 |
| Deseases | BT | 0.0 ± 0.0 | 0.0 ± 0.0 | 0.0-0.0 |
| Insects | BT | 0.0 ± 0.0 | 0.0 ± 0.0 | 0.0-0.0 |
| Deseases | FL | 0.0 ± 0.0 | 0.0 ± 0.0 | 0.0-0.0 |
| Insects | FL | 0.0 ± 0.0 | 0.0 ± 0.0 | 0.0-0.0 |
| Insects | ET | 0.0 ± 0.0 | 0.0 ± 0.0 | 0.0-0.0 |

VRn: rosette;
BT: floral bud;
FL: flowering;
ET: stem elongation;
MF: physiological mature

Conclusions

The results presented of the agronomic traits and the interaction of the molecular stack of safflower events with the environment confirm the agronomic equivalence of the transgenic event with the control and with the commercial varieties grown in parallel. Therefore, no adverse effects are expected from the presence of IND-10003-4 X IND-10015-7 or the use of varieties derived from it, while molecular stacking of safflower events results in higher levels of chymosin expression.

Having especially described and determined the nature of the present invention and having explained how to implement it, we claim the exclusive property right on:

1. A pair of DNA primer molecules comprising a first DNA molecule and a second DNA molecule different from the first DNA molecule,
wherein the first and the second DNA molecules each consists of the nucleotide sequence selected from SEQ ID NOs: 8, 9, 11-14, 16-18, and the complements thereof,
wherein when used together in an amplification reaction with DNA from a plant comprising SEQ ID NO: 1 and 2, the pair of DNA primer molecules produces an amplicon diagnostic for the plant comprising SEQ ID NO: 1 and 2.

2. A set of primer molecules comprising:
(a) a first primer molecule having a nucleotide sequence consisting of SEQ ID NO: 16, a second primer molecule having a nucleotide sequence consisting of SEQ ID NO: 17, and a third primer molecule having a nucleotide sequence consisting of SEQ ID NO: 18,
or
(b) a first primer molecule having a nucleotide sequence consisting of SEQ ID NO: 11, a second primer molecule having a nucleotide sequence consisting of SEQ ID NO: 12, and a third primer molecule having a nucleotide sequence consisting of SEQ ID NO: 13.

3. A DNA detection kit comprising the set of primer molecules of claim 2 and instructions for use in DNA detection.

* * * * *